US012636295B2

(12) United States Patent
Bleackley et al.

(10) Patent No.: US 12,636,295 B2
(45) Date of Patent: May 26, 2026

(54) COMPOSITIONS AND METHODS FOR THE TREATMENT OF OBSTRUCTIVE SLEEP APNOEA (OSA)

(71) Applicant: Incannex Healthcare Limited, Norwest (AU)

(72) Inventors: Mark Robert Bleackley, South Morang (AU); Sudhanshu Agarwal, Toorak (AU); Joel Bradley Latham, North Kellyville (AU)

(73) Assignee: Incannex Healthcare Limited, Norwest (AU)

( * ) Notice: Subject to any disclaimer, the term of this patent is extended or adjusted under 35 U.S.C. 154(b) by 574 days.

(21) Appl. No.: 18/000,880

(22) PCT Filed: Jul. 9, 2021

(86) PCT No.: PCT/AU2021/050734

§ 371 (c)(1),
(2) Date: Dec. 6, 2022

(87) PCT Pub. No.: WO2022/006636

PCT Pub. Date: Jan. 13, 2022

(65) Prior Publication Data

US 2023/0310364 A1 Oct. 5, 2023

(30) Foreign Application Priority Data

Jul. 9, 2020 (AU) ................................ 2020902368

(51) Int. Cl.
*A61K 31/00* (2006.01)
*A61K 31/433* (2006.01)
*A61P 11/00* (2006.01)

(52) U.S. Cl.
CPC .......... *A61K 31/658* (2023.05); *A61K 31/433* (2013.01); *A61P 11/00* (2018.01)

(58) Field of Classification Search
CPC ............................ A61K 31/352; A61K 31/658
See application file for complete search history.

(56) References Cited

U.S. PATENT DOCUMENTS

| | | | | |
|---|---|---|---|---|
| 2017/0348303 | A1 | 12/2017 | Bosse et al. | |
| 2022/0000833 | A1 * | 1/2022 | Zuloff-Shani | A61P 21/00 |
| 2024/0189328 | A1 * | 6/2024 | Miller | A61K 31/352 |

FOREIGN PATENT DOCUMENTS

| | | | |
|---|---|---|---|
| WO | WO 2019/071302 | A1 | 4/2019 |
| WO | WO 2019/180706 | A1 | 9/2019 |

OTHER PUBLICATIONS

Sullivan et al., Expert Opinion on Emerging Drugs, 2015, 20(4): 571-582.*
Calik, M. W., "Treatments for Obstructive Sleep Apnea", Journal of Clinical Outcomes Management, (Apr. 2016), vol. 23, No. 4, pp. 181-192.
Gaisl, T. et al., "Efficacy ofpharmacotherapy for OSA in adults: A systematic review and network meta-analysis", Sleep Medicine Reviews, (Apr. 2019), vol. 46, pp. 74-86.
Sullivan, S. S. & Guilleminault, C., "Emerging drugs for common conditions of sleepiness: obstructive sleep apnea and narcolepsy", Expert Opinion on Emerging Drugs, (2015), vol. 20, No. 4, pp. 571-582.
Carley, David W., et al. "Pharmacotherapy of Apnea by Cannabimimetic Enhancement, the PACE Clinical Trial: Effects of Dronabinol in Obstructive Sleep Apnea." Sleep 41, No. 1 (2018).
Edwards, Bradley A., et al. "Acetazolamide Attenuates The Ventilatory Response To Arousal In Patients With Obstructive Sleep Apnea." Sleep 36.2 (2013): 281-285.
Notification of Reasons for Rejection received in Japanese Patent Application No. 2023-501090, dated Jul. 30, 2025.
Extended European Search Report received in European Patent Application No. 21837113.6, dated Sep. 18, 2024.
Notice of Allowance on Japanese Patent Application No. 2023-501090, dated Dec. 1, 2025.

* cited by examiner

*Primary Examiner* — Rei Tsang Shiao
(74) *Attorney, Agent, or Firm* — Knobbe Martens Olson & Bear LLP

(57) ABSTRACT

Compositions including Δ-9-tetrahydrocannabinol (THC) and a carbonic andydrase inhibitor and methods of using these compositions for the treatment of obstructive sleep apnoea (OSA). The treatment method also includes administering dronabinol and acetazolaminde and combinations thereof to a subject in need thereof.

15 Claims, 2 Drawing Sheets

COMPOSITIONS AND METHODS FOR THE TREATMENT OF OBSTRUCTIVE SLEEP APNOEA (OSA)

FIELD

The present disclosure relates generally to compositions and methods for the treatment of obstructive sleep apnoea (OSA).

RELATED APPLICATIONS

This application claims priority from Australian Provisional Patent Application No. 2020902368 filed on 9 Jul. 2020, the entire content of which is hereby incorporated by reference.

BACKGROUND

Obstructive sleep apnoea (OSA) is characterised by a narrowing or obstruction of the upper airway in sleep. This relatively common in chronic disorder is largely undiagnosed and untreated, it can result in a wide range of serious long-term outcomes, including cardiovascular disease (Drager et al., 2017*, Circulation,* 136(19): 1840-1850), cognitive impairments such as memory loss, poor concentration and judgement (Olaithe et al., 2018, *Sleep Medicine Reviews,* 38: 39-49), depression (Wheaton et al., 2012*, Sleep,* 35(4): 461-467) and death or injury due to traffic accidents (Stoohs et al., 1994*, Sleep,* 17(7): 619-623). The costs associated with OSA are substantial, relating to lost productivity, workplace and motor vehicle accidents (Sleep Health Foundation, 2017). It was recently estimated that OSA affects some 936 million adults worldwide, which is expected to increase due to growing prevalence of obesity and an ageing global population (Benjafiled et al., 2018, *Risk and Prevalence of Sleep Disordered Breathing*: A3962-A3962; Grote, 2019*, The Lancet Respiratory Medicine,* 7(8): 645-647).

Current standard of care for the treatment of OSA is continuous positive airway pressure (CPAP); however, this therapy has several drawbacks. It can be cumbersome, expensive and is often poorly adhered to, which significantly reduces efficacy. Therefore, while CPAP has a high success rate, high levels of patient discomfort leads to low compliance, poor tolerability and low long-term adherence in patients. Further, while medications and supplements have been used with varying success to treat insomnia and poor sleep quality, pharmacotherapy for OSA has little success, and effective agents are yet to be identified. Therefore, there remains an urgent need for the development of pharmacological approaches for the treatment of OSA.

SUMMARY

In an aspect of the present disclosure, there is provided a method for the treatment of obstructive sleep apnoea (OSA), the method comprising administering to a subject in need thereof Δ-9-tetrahydrocannabinol (THC) or a pharmaceutically acceptable salt thereof, and a carbonic anhydrase inhibitor or a pharmaceutically acceptable salt thereof.

In another aspect of the present disclosure, there is provided a use of THC or a pharmaceutically acceptable salt thereof, and a carbonic anhydrase inhibitor or a pharmaceutically acceptable salt thereof, in the manufacture of a medicament for the treatment of OSA.

In another aspect of the present disclosure, there is provided a kit comprising THC or a pharmaceutically acceptable salt thereof, and a carbonic anhydrase inhibitor or a pharmaceutically acceptable salt thereof for use in the treatment of OSA.

In another aspect of the present disclosure, there is provided a composition comprising THC or a pharmaceutically acceptable salt thereof, and a carbonic anhydrase inhibitor or a pharmaceutically acceptable salt thereof.

BRIEF DESCRIPTION OF THE FIGURES

Various examples and embodiments of the invention are described herein, by way of non-limiting example only, with reference to the following figures.

DETAILED DESCRIPTION

Figure 1:
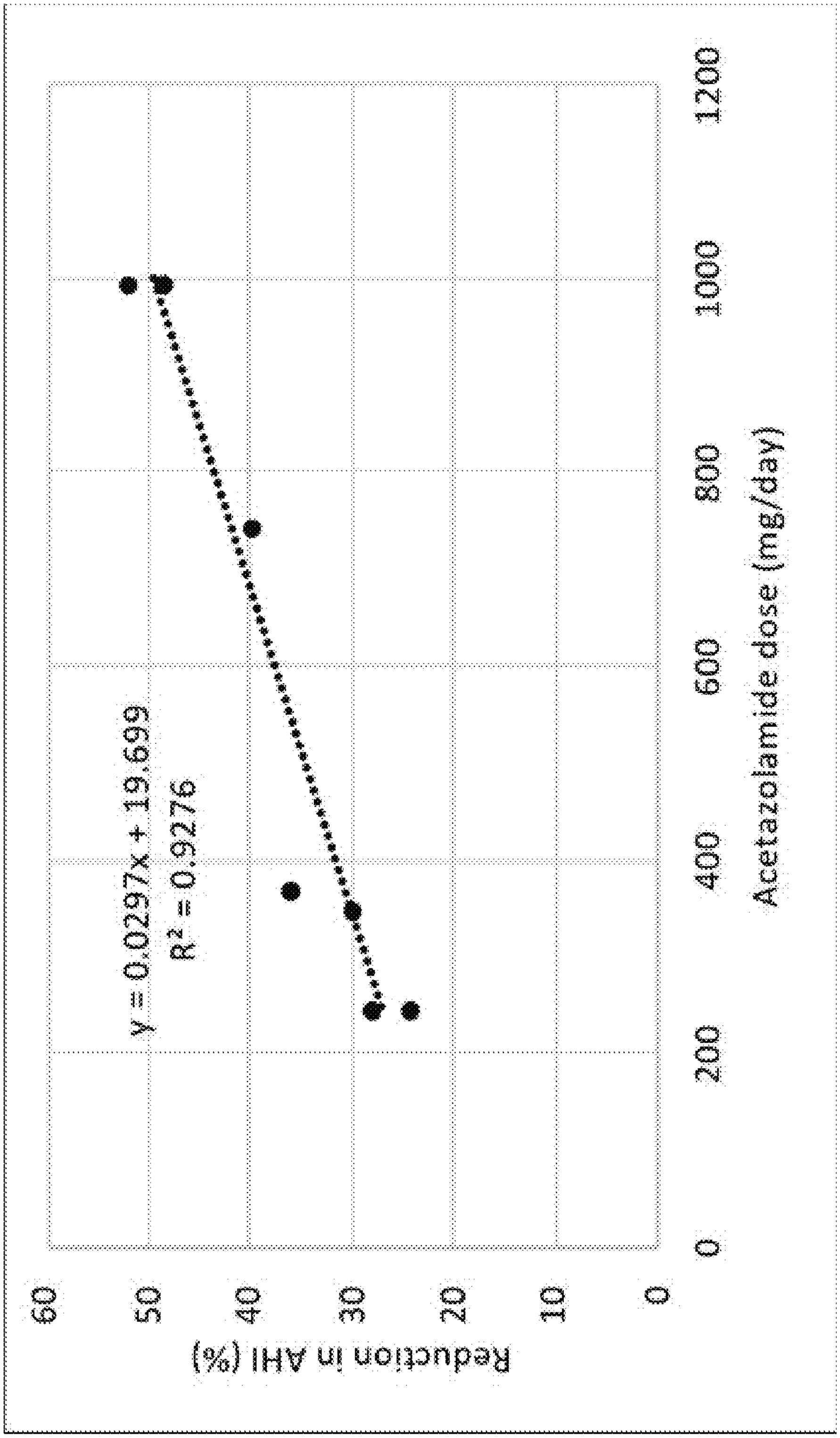
FIG. 1 is a graphical representation of dose response to acetazolamide (mg/day; x-axis) and reduction in Apnoea Hypopnoea Index (AHI) relative to baseline or placebo (%; y-axis).

Unless defined otherwise, all technical and scientific terms used herein have the same meaning as commonly understood by those of ordinary skill in the art to which the disclosure belongs. Any materials and method similar or equivalent to those described herein can be used to practice the present invention.

Throughout this specification, unless the context requires otherwise, the word "comprise", or variations such as "comprises" or "comprising", will be understood to imply the inclusion of the stated element or integer or group of elements or integers but not the exclusion of any other element or integer or group of elements or integers.

The phrase "consisting of" means including, and limited to, whatever follows the phrase "consisting of". Thus, the phrase "consisting of" indicates that the listed elements are required or mandatory, and that no other elements may be present. The phrase "consisting essentially of" means including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein the singular forms "a", "an" and "the" include plural aspects unless the context clearly dictates otherwise. Thus, for example, reference to "a compound" includes a single compound, as well as two or more compounds; reference to "an agent" includes one agent, as well as two or more agents; and so forth.

The term "about" will be understood by persons skilled in the art and will vary to some extent depending on the context in which it is used. If there are uses of the term that are not clear to persons skilled in the art, given the context which it is used, "about" will mean up to plus or minus 10% of the particular term.

The present disclosure is predicated, at least in part, on the surprising finding that Δ-9-tetrahydrocannabinol (THC) or a pharmaceutically acceptable salt thereof and a carbonic anhydrase inhibitor or a pharmaceutically acceptable salt thereof can synergize to stabilize the respiratory patterns of patients with obstructive sleep apnoea (OSA).

Thus, in an aspect disclosed herein, there is provided a method for the treatment of OSA, the method comprising administering to a subject in need thereof THC or a pharmaceutically acceptable salt thereof, and a carbonic anhydrase inhibitor or a pharmaceutically acceptable salt thereof.

Sleep Apnoea

The term "sleep apnoea" as used herein refers to sleep disorders characterized by episodes of interrupted breathing during sleep, which results in decreased oxygen saturation or arousal from sleep. This disturbance results in fragmented, non-restorative sleep, typically accompanied by other symptoms including loud, disruptive snoring, witnessed apnoeas during sleep and excessive daytime sleepiness.

The term "apnoea" as used herein refers to a complete or near complete cessation of airflow for at least 10 seconds followed by an arousal and/or >4% oxygen desaturation.

The term "hypopnoea" as used herein refers to 30% or greater decrease in airflow for at least 10 seconds followed by an arousal and/or >4% oxygen desaturation.

"Obstructive sleep apnoea" or "OSA" is characterized by episodes of complete collapse of the airway or partial collapse with an associated decrease in oxygen saturation or arousal from sleep.

OSA may be classified using the apnoea-hypopnoea index (AHI) or respiratory disturbance index (RDI) as described by, e.g., Iber et al. (2007, *The AASM Manual for the Scoring of Sleep and Associated Events,* $1^{st}$ edition), which is based on the average number of obstructive events per hour. Methods for the measurement of obstructive events would be known to persons skilled in the art, illustrative embodiments of which include overnight polysomnography (PSG).

The terms "overnight polysomnography", "overnight PSG", "nocturnal polysomnography", or "nocturnal PSG" may be used interchangeably herein to refer to a test used in the diagnosis of OSA. Overnight PSG consists of a simultaneous recording of multiple physiologic parameters related to sleep and wakefulness. The physiological parameters recorded during PSG would be known to persons skilled in the art, illustrative examples of which include brain activity (e.g., electroencephalogram (EEG)), eye movements (e.g., electroculogram (EOG)), muscle activity of the jaw and legs (e.g., electromyogram (EMG)), heart rhythm (electrocardiogram (ECG)), respiratory airflow (e.g., via a nasal cannula and thermistor), respiratory effort (e.g., via abdominal and thoracic respiratory bands) and peripheral pulse oximetry (e.g., via an infrared finger probe). From these parameters, OSA-related indices can be measured, including sleep onset latency, REM-sleep onset latency, the number of awakening during the sleep period, the total sleep duration, percentages and durations of every sleep stage, number of arousals, the AHI and arterial oxygen saturation.

According to the AHI, the severity of OSA may be classified as none/minimal, mild, moderate or severe (Table 1).

TABLE 1

Classification of OSA according to Apnoea-Hypopnoea Index (AHI)

| Classification | Number of Events/ hour (AHI) |
|---|---|
| None/minimal | <5 |
| Mild | ≥5 and <15 |
| Moderate | ≥15 and ≤30 |
| Severe | >30 |

Classification of children with OSA may be performed using modified classification thresholds, with mild OSA defined as an AHI of >1 and <5 if one or more of the clinical symptoms of OSA have been reported; moderate OSA defined as an AHI of ≥5 and <10; and severe OSA defined as an AHI of ≥10.

In an embodiment, the OSA is mild to severe OSA according to the AHI. In another embodiment, the OSA is moderate to severe OSA according to the AHI.

The classification of OSA based on the AHI may also be made in consideration of clinical symptoms, such as excessive daytime sleepiness, sleep maintenance insomnia and cognitive dysfunction. For example, an AHI of 5 to 14.9 is classified as mild OSA if one or more of the clinical symptoms of OSA has been reported.

Tetrahydrocannabinol (THC)

"Δ-9-tetrahydrocannabinolic acid" or "THCA" is synthesized in *cannabis* plants from the cannabigerolic acid (CBGA) precursor by THCA synthase (Table 2). THCA decarboxylates to the neutral form "Δ-9-tetrahydrocannabinol" or "THC", which is associated with psychoactive effects of *cannabis* as primarily mediated by its activation of CB1G-protein coupled receptors, which result in a decrease in the concentration of cyclic AMP (cAMP) through the inhibition of adenylate cyclase. THC also exhibits partial agonist activity at the cannabinoid receptors CB1 and CB2. CB1 is mainly associated with the central nervous system, while CB2 is expressed predominantly in the cells of the immune system. As a result, THC is also associated with pain relief, relaxation, fatigue, appetite stimulation, and alteration of the visual, auditory and olfactory senses. Furthermore, more recent studies have indicated that THC mediates an anti-cholinesterase action, which may suggest its use for the treatment of Alzheimer's disease and myasthenia (Eubanks et al., 2006, *Molecular Pharmaceuticals,* 3(6): 773-7).

TABLE 2

Tetrahydrocannabinol and related cannabinoids

| Name | Structure | Chemical properties/ $[M + H]^+$ ESI MS |
|---|---|---|
| Dronabinol | 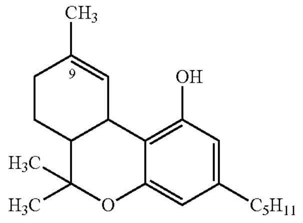 | Synthetic enantiomer form of $\Delta^9$-THC m/z 314.46 |
| Δ-9-tetrahydrocannabinol (THC) | 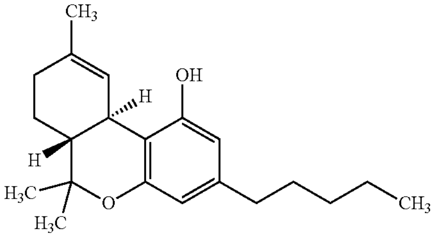 [SMILES: CCCCCc1cc(O)c2c(c1)OC(C)(C)[C@@H]1CCC(C)=C[C@@H]21] | Psychoactive, decarboxylation product of THCA m/z 314.46 |
| Δ9-tetrahydrocannabinolic acid (THCA) | 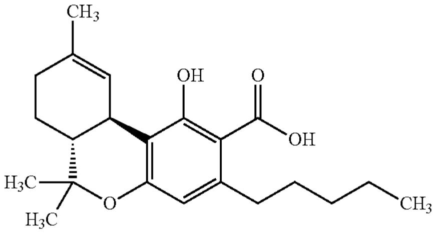 [SMILES: CCCCCc1cc2c(c(O)c1C(=O)O)[C@@H]1C=C(C)CC[C@H]1C(C)(C)O2] | m/z 359.2217 |
| cannabigerolic acid (CBGA) | 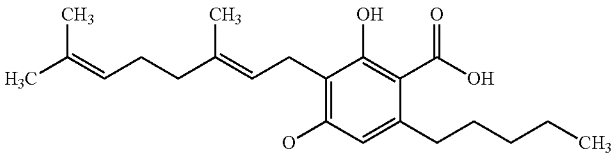 [SMILES: CCCCCc1cc(O)c(C/C=C(\C)CCC=C(C)C)c(O)c1C(=O)O] | m/z 361.2373 |

THC may be extracted from any suitable plant parts including leaves, flowers or stems and may be produced by any suitable means known to those skilled in the art. For example, THC extracts may be produced by extraction with supercritical or subcritical $CO_2$, or by volatilization of plant material with a heated gas. Illustrative examples of methods used the extract THC and other cannabinoids from plant material include the methods described in U.S. patent Ser. No. 10/189,762 and WO 2004/016277.

In an embodiment, the THC described herein is synthetic THC. In a preferred embodiment, the THC is dronabinol.

Dronabinol is commercially available in capsule form under the trade name Marinol from AbbVie and one or more manufacturers, distributors, and/or repackaged under a generic (i.e., non-proprietary) name. Dronabinol is also commercially available in liquid form under the trade name Syndros from Insys.

Synthetic THC is particularly useful for pharmaceutical development as it can be prepared largely free from contaminants A number of methods for the synthesis of THC are known in the art, illustrative examples of which include methods for the synthesis of dronabinol as described in U.S. Pat. Nos. 7,323,576 and 5,227,537, and U.S. patent application Ser. No. 11/840,585.

The present disclosure further contemplates the use of a pharmaceutically acceptable salt of THC. Suitable pharmaceutically acceptable salts of THC would be known to persons skilled in the art, illustrative examples of which include salts or esters prepared from pharmaceutically acceptable non-toxic bases or acids, including inorganic bases or acids and organic bases or acids, which would be known to persons skilled in the art.

Carbonic Anhydrase Inhibitors

As used herein, the term "carbonic anhydrase inhibitor" refers to a class of agents that inhibit the activity of carbonic anhydrase, an enzyme responsible for catalyzing the reaction between carbon dioxide and water into carbonic acid and subsequently to bicarbonate. The suppression of carbonic anhydrase activity leads to metabolic acidosis, and as a result, increases ventilation and oxygenation. Carbonic anhydrase inhibitors are used in the treatment or prevention of acute mountain sickness (i.e., altitude sickness), as described by Swenson (2014, *Carbonic Anhydrase Inhibitors and High Altitude Illness*, in: Frost and McKenna (eds), *Carbonic Anhydrase: Mechanism, Regulation, Links to Disease, and Industrial Applications. Subcellular Biochemistry, vol.* 75, Springer, Dordrecht). Suitable carbonic anhydrase inhibitors will be known to persons skilled in the art, illustrative examples of which include acetazolamide, methazolamide, dorolamide and brinzolamide.

In an embodiment, the carbonic anhydrase inhibitor is selected from the group consisting of acetazolamide, methazolamide, dorolamide and brinzolamide. In another embodiment, the carbonic anhydrase inhibitor is a sulfonamide, a member of thiadiazoles and a monocarboxylic acid amide, or pharmaceutically acceptable salts thereof.

In a preferred embodiment, the carbonic anhydrase inhibitor is acetazolamide.

The present disclosure further contemplates the use of a pharmaceutically acceptable salt of the carbonic anhydrase inhibitor. Suitable pharmaceutically acceptable salts of the carbonic anhydrase inhibitor would be known to person skilled in the art, illustrative examples of which include salts or esters prepared from pharmaceutically acceptable non-toxic bases or acids, including inorganic bases or acids and organic bases or acids, which would be well known to person skilled in the art.

Methods for the Treatment of Sleep Apnoea

The terms "treat", "treating", "treatment" and the like are used interchangeably herein to mean relieving, reducing, alleviating, ameliorating or otherwise inhibiting the severity of one or more symptoms of OSA in a subject. It is to be understood that the terms "treat", "treating", "treatment" and the like, as used herein, do not imply that a subject is treated until the OSA has been eliminated or are no longer evident. Said treatment may also reduce the severity of the one or more symptoms of OSA.

The term "subject" as used herein refers to any mammal, including livestock and other farm animals (such as cattle, goats, sheep, horses, pigs and chickens), performance animals (such as racehorses), companion animals (such as cats and dogs), laboratory test animals and humans. In an embodiment, the subject is a human.

It is to be understood that the THC or a pharmaceutically acceptable salt thereof, and the carbonic anhydrase inhibitor or a pharmaceutically acceptable salt thereof will be administered to the subject in need thereof in a therapeutically effective amount. As used herein, the term "therapeutically effective amount" typically refers to an amount of THC and an amount of carbonic anhydrase inhibitor that is sufficient to affect one or more beneficial or desired therapeutic outcomes (e.g., reduction in apnoeic episodes, reduction in hypopnoeic episodes, reduction in AHI, reduction in excessive daytime sleepiness, reduction in oxygen desaturation index (ODI), improvement in mood and well-being). Said beneficial or desired therapeutic outcomes may be quantified by measuring clinical parameters, illustrative examples of which include the measurement of arterial oxygen saturation ($SaO_2$) as described by Zamarron et al. (2003, *Chest,* 123(5): 1567-1576), movement of the chest and abdomen measured by inductance plethysmograph as described by Kogan et al. (2016, *Respiratory Care,* 61(8): 1033-1037), nasal airflow as described by de Souse Michels et al. (2014, *International Journal of Otolaryngology,* 2014: 717419) and heart rate spectral analysis as described by Roche et al. (2003, *European Respiratory Journal,* 22: 937-942). Subjective measures of sleep quality improvement can also be made using clinical instruments known in the art, illustrative examples of this include the Epworth Sleepiness Scale (ESS) (Johns, 1991, *Sleep,* 14: 540-545), the Leeds Sleep Evaluation Questionnaire (LSEQ) (Shahid et al., 2011, *Leeds Sleep Evaluation Questionnaire* (LSEQ), in Shahid et al. (eds), STOP, *THAT and One Hundred Other Sleep Scales, Springer*, New York), the Profile of Mood States (POMS) (McNair et al., 1971, *POMS Manual for the Profile of Mood States*, San Diego, CA: Educational and Industrial Testing Service), Short Form-36 (SF-36) (Saris-Baglama et al., 2010, *QualityMetric Health Outcomes Scoring Software* 4.0, Lincoln, RI) and the Pittsburgh Sleep Quality Index (PSQI) (Buysse et al., 1989, *Psychiatry Research,* 28(2): 193-213).

Changes in the symptoms or severity of OSA as measured by any of the quantitative methods or clinical instruments described elsewhere herein may be expressed using any appropriate statistical measure to demonstrate the magnitude of the reduction in the symptoms or severity of OSA. In an embodiment, the methods disclosed herein reduce in the symptoms or severity of OSA by at least 10%, preferably at least 20%, preferably at least 30%, preferably at least 40%, preferably at least 50%, preferably at least 60%, preferably at least 70%, preferably at least 80%, preferably at least 90%, or more preferably at least 100% as compared to a subject with OSA who has not been administered THC or a pharmaceutically acceptable salt thereof, and a carbonic anhydrase inhibitor or a pharmaceutically acceptable salt thereof.

In an embodiment, the methods disclosed herein are useful in reducing the AHI in subjects with OSA.

In an embodiment, the methods disclosed herein are useful in reducing the AHI in subjects with OSA by >20% as compared to a subject with OSA who has not been administered THC or a pharmaceutically acceptable salt thereof, and a carbonic anhydrase inhibitor or a pharmaceutically acceptable salt thereof.

An effective amount can be provided in one or more administrations. The exact amount required may vary depending on factors such as the nature and severity of the OSA to be treated, the age and general health of the subject, and the form in which the active agents are to be administered.

In an embodiment, the carbonic anhydrase inhibitor or a pharmaceutically acceptable salt thereof is administered at a dose of from about 1 mg to about 700 mg (e.g., 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 131 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 434 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, 465 mg, 466 mg, 467 mg, 468 mg, 469 mg, 470 mg, 471 mg, 472 mg, 473 mg, 474 mg, 475 mg, 476 mg, 477 mg, 478 mg, 479 mg, 480 mg, 481 mg, 482 mg, 483 mg, 484 mg, 485 mg, 486 mg, 487 mg, 488 mg, 489 mg, 490 mg, 491 mg, 492 mg, 493 mg, 494 mg, 495 mg, 496 mg, 497 mg, 498 mg, 499 mg, 500 mg, 501 mg, 502 mg, 503 mg, 504 mg, 505 mg, 506 mg, 507 mg, 508 mg, 509 mg, 510 mg, 511 mg, 512 mg, 513 mg, 514 mg, 515 mg, 516 mg, 517 mg, 518 mg, 519 mg, 520 mg, 521 mg, 522 mg, 523 mg, 524 mg, 525 mg, 526 mg, 527 mg, 528 mg, 529 mg, 530 mg, 531 mg, 532 mg, 535 mg, 534 mg, 535 mg, 536 mg, 537 mg, 538 mg, 539 mg, 540 mg, 541 mg, 542 mg, 543 mg, 544 mg, 545 mg, 546 mg, 547 mg, 548 mg, 549 mg, 550 mg, 551 mg, 552 mg, 553 mg, 554 mg, 555 mg, 556 mg, 557 mg, 558 mg, 559 mg, 560 mg, 561 mg, 562 mg, 563 mg, 564 mg, 565 mg, 566 mg, 567 mg, 568 mg, 569 mg, 570 mg, 571 mg, 572 mg, 573 mg, 574 mg, 575 mg, 576 mg, 577 mg, 578 mg, 579 mg, 580 mg, 581 mg, 582 mg, 583 mg, 584 mg, 585 mg, 586 mg, 587 mg, 588 mg, 589 mg, 590 mg, 591 mg, 592 mg, 593 mg, 594 mg, 595 mg, 596 mg, 597 mg, 598 mg, 599 mg, 600 mg, 601 mg, 602 mg, 603 mg, 604 mg, 605 mg, 606 mg, 607 mg, 608 mg, 609 mg, 610 mg, 611 mg, 612 mg, 613 mg, 614 mg, 615 mg, 616 mg, 617 mg, 618 mg, 619 mg, 620 mg, 621 mg, 622 mg, 623 mg, 624 mg, 625 mg, 626 mg, 627 mg, 628 mg, 629 mg, 630 mg, 631 mg, 632 mg, 636 mg, 634 mg, 635 mg, 636 mg, 637 mg, 638 mg, 639 mg, 640 mg, 641 mg, 642 mg, 643 mg, 644 mg, 645 mg, 646 mg, 647 mg, 648 mg, 649 mg, 650 mg, 651 mg, 652 mg, 653 mg, 654 mg, 655 mg, 656 mg, 657 mg, 658 mg, 659 mg, 660 mg, 661 mg, 662 mg, 663 mg, 664 mg, 665 mg, 666 mg, 667 mg, 668 mg, 669 mg, 670 mg, 671 mg, 672 mg, 673 mg, 674 mg, 675 mg, 676 mg, 677 mg, 678 mg, 679 mg, 680 mg, 681 mg, 682 mg, 683 mg, 684 mg, 685 mg, 686 mg, 687 mg, 688 mg, 689 mg, 690 mg, 691 mg, 692 mg, 693 mg, 694 mg, 695 mg, 696 mg, 697 mg, 698 mg, 699 mg or 700 mg)

Thus, in an embodiment the carbonic anhydrase inhibitor or a pharmaceutically acceptable salt thereof is administered at a dose of from about 1 mg to about 700 mg, preferably about 1 mg, preferably about 2 mg, preferably about 3 mg, preferably about 4 mg, preferably about 5 mg, preferably about 6 mg, preferably about 7 mg, preferably about 8 mg, preferably about 9 mg, preferably about 10 mg, preferably about 11 mg, preferably about 12 mg, preferably about 13 mg, preferably about 14 mg, preferably about 15 mg, preferably about 16 mg, preferably about 17 mg, preferably about 18 mg, preferably about 19 mg, preferably about 20 mg, preferably about 21 mg, preferably about 22 mg, preferably about 23 mg, preferably about 24 mg, preferably about 25 mg, preferably about 26 mg, preferably about 27 mg, preferably about 28 mg, preferably about 29 mg, preferably about 30 mg, preferably about 31 mg, preferably about 32 mg, preferably about 33 mg, preferably about 34 mg, preferably about 35 mg, preferably about 36 mg, preferably about 37 mg, preferably about 38 mg, preferably about 39 mg, preferably about 40 mg, preferably about 41 mg, preferably about 42 mg, preferably about 43 mg, preferably about 44 mg, preferably about 45 mg, preferably about 46 mg, preferably about 47 mg, preferably about 48 mg, preferably about 49 mg, preferably about 50 mg, preferably about 51 mg, preferably about 52 mg, preferably about 53 mg, preferably about 54 mg, preferably about 55 mg, preferably about 56 mg, preferably about 57 mg, preferably about 58 mg, preferably about 59 mg, preferably about 60 mg, preferably about 61 mg, preferably about 62 mg, preferably about 63 mg, preferably about 64 mg, preferably about 65 mg, preferably about 66 mg, preferably about 67 mg, preferably about 68 mg, preferably about 69 mg, preferably about 70 mg, preferably about 71 mg, preferably about 72 mg, preferably about 73 mg, preferably about 74 mg, preferably about 75 mg, preferably about 76 mg, preferably about 77 mg, preferably about 78 mg, preferably about 79 mg, preferably about 80 mg, preferably about 81 mg, preferably about 82 mg, preferably about 83 mg, preferably about 84 mg, preferably about 85 mg, preferably about 86 mg, preferably about 87 mg, preferably about 88 mg, preferably about 89 mg, preferably about 90 mg, preferably about 91 mg, preferably about 92 mg, preferably about 93 mg, preferably about 94 mg, preferably about 95 mg, preferably about 96 mg, preferably about 97 mg, preferably about 98 mg, preferably about 99 mg, preferably about 100 mg, preferably about 101 mg, preferably about 102 mg, preferably about 103 mg, preferably about 104 mg, preferably about 105 mg, preferably about 106 mg, preferably about 107 mg, preferably about 108 mg, preferably about 109 mg, preferably about 110 mg, preferably about 111 mg, preferably about 112 mg, preferably about 113 mg, preferably about 114 mg, preferably about 115 mg, preferably about 116 mg, preferably about 117 mg, preferably about 118 mg, preferably about 119 mg, preferably about 120 mg, preferably about 121 mg, preferably about 122 mg, preferably about 123 mg, preferably about 124 mg, preferably about 125 mg, preferably about 126 mg, preferably about 127 mg, preferably about 128 mg, preferably about 129 mg, preferably about 130 mg, preferably about 131 mg, preferably about 132 mg, preferably about 131 mg, preferably about 134 mg, preferably about 135 mg, preferably about 136 mg, preferably about 137 mg, preferably about 138 mg, preferably about 139 mg, preferably about 140 mg, preferably about 141 mg, preferably about 142 mg, preferably about 143 mg, preferably about 144 mg, preferably about 145 mg, preferably about 146 mg, preferably about 147 mg, preferably about 148 mg, preferably about 149 mg, preferably about 150 mg, preferably about 151 mg, preferably about 152 mg, preferably about 153 mg, preferably about 154 mg, preferably about 155 mg, preferably about 156 mg, preferably about 157 mg, preferably about 158 mg, preferably about 159 mg, preferably about 160 mg, preferably about 161 mg, preferably about 162 mg, preferably about 163 mg, preferably about 164 mg, preferably about 165 mg, preferably about 166 mg, preferably about 167 mg, preferably about 168 mg, preferably about 169 mg, preferably about 170 mg, preferably about 171 mg, preferably about 172 mg, preferably about 173 mg, preferably about 174 mg, preferably about 175 mg, preferably about 176 mg, preferably about 177 mg, preferably about 178 mg, preferably about 179 mg, preferably about 180 mg, preferably about 181 mg, preferably about 182 mg, preferably about 183 mg, preferably about 184 mg, preferably about 185 mg, preferably about 186 mg, preferably about 187 mg, preferably about 188 mg, preferably about 189 mg, preferably about 190 mg, preferably about 191 mg, preferably about 192 mg, preferably about 193 mg, preferably about 194 mg, preferably about 195 mg, preferably about 196 mg, preferably about 197 mg, preferably about 198 mg, preferably about 199 mg, preferably about 200 mg, preferably about 201 mg, preferably about 202 mg, preferably about 203 mg, preferably about 204 mg, preferably about 205 mg, preferably about 206 mg, preferably about 207 mg, preferably about 208 mg, preferably about 209 mg, preferably about 210 mg, preferably about 211 mg, preferably about 212 mg, preferably about 213 mg, preferably about 214 mg, preferably about 215 mg, preferably about 216 mg, preferably about 217 mg, preferably about 218 mg, preferably about 219 mg, preferably about 220 mg, preferably about 221 mg, preferably about 222 mg, preferably about 223 mg, preferably about 224 mg, preferably about 225 mg, preferably about 226 mg, preferably about 227 mg, preferably about 228 mg, preferably about 229 mg, preferably about 230 mg, preferably about 231 mg, preferably about 232 mg, preferably about 233 mg, preferably about 234 mg, preferably about 235 mg, preferably about 236 mg, preferably about 237 mg, preferably about 238 mg, preferably about 239 mg, preferably about 240 mg, preferably about 241 mg, preferably about 242 mg, preferably about 243 mg, preferably about 244 mg, preferably about 245 mg, preferably about 246 mg, preferably about 247 mg, preferably about 248 mg, preferably about 249 mg, preferably about 250 mg, preferably about 251 mg, preferably about 252 mg, preferably about 253 mg, preferably about 254 mg, preferably about 255 mg, preferably about 256 mg, preferably about 257 mg, preferably about 258 mg, preferably about 259 mg, preferably about 260 mg, preferably about 261 mg, preferably about 262 mg, preferably about 263 mg, preferably about 264 mg, preferably about 265 mg, preferably about 266 mg, preferably about 267 mg, preferably about 268 mg, preferably about 269 mg, preferably about 270 mg, preferably about 271 mg, preferably about 272 mg, preferably about 273 mg, preferably about 274 mg, preferably about 275 mg, preferably about 276 mg, preferably about 277 mg, preferably about 278 mg, preferably about 279 mg, preferably about 280 mg, preferably about 281 mg, preferably about 282 mg, preferably about 283 mg, preferably about 284 mg, preferably about 285 mg, preferably about 286 mg, preferably about 287 mg, preferably about 288 mg, preferably about 289 mg, preferably about 290 mg, preferably about 291 mg, preferably about 292 mg, preferably about 293 mg, preferably about 294 mg, preferably about 295 mg, preferably about 296 mg, preferably about 297 mg, preferably about 298 mg, preferably about 299 mg, preferably about 300 mg, preferably about 301 mg, preferably about 302 mg, preferably about 303 mg, preferably about 304 mg, preferably about 305 mg, preferably about 306 mg, preferably about 307 mg, preferably about 308 mg, preferably about 309 mg, preferably about 310 mg, preferably about 311 mg, preferably about 312 mg, preferably about 313 mg, preferably about 314 mg, preferably about 315 mg, preferably about 316 mg, preferably about 317 mg, preferably about 318 mg, preferably about 319 mg, preferably about 320 mg, preferably about 321 mg, preferably about 322 mg, preferably about 323 mg, preferably about 324 mg, preferably about 325 mg, preferably about 326 mg, preferably about 327 mg, preferably about 328 mg, preferably about 329 mg, preferably about 330 mg, preferably about 331 mg, preferably about 332 mg, preferably about 333 mg, preferably about 334 mg, preferably about 335 mg, preferably about 336 mg, preferably about 337 mg, preferably about 338 mg, preferably about 339 mg, preferably about 340 mg, preferably about 341 mg, preferably about 342 mg, preferably about 343 mg, preferably about 344 mg, preferably about 345 mg, preferably about 346 mg, preferably about 347 mg, preferably about 348 mg, preferably about 349 mg, preferably about 350 mg, preferably about 351 mg, preferably about 352 mg, preferably about 353 mg, preferably about 354 mg, preferably about 355 mg, preferably about 356 mg, preferably about 357 mg, preferably about 358 mg, preferably about 359 mg, preferably about 360 mg, preferably about 361 mg, preferably about 362 mg, preferably about 363 mg, preferably about 364 mg, preferably about 365 mg, preferably about 366 mg, preferably about 367 mg, preferably about 368 mg, preferably about 369 mg, preferably about 370 mg, preferably about 371 mg, preferably about 372 mg, preferably about 373 mg, preferably about 374 mg, preferably about 375 mg, preferably about 376 mg, preferably about 377 mg, preferably about 378 mg, preferably about 379 mg, preferably about 380 mg, preferably about 381 mg, preferably about 382 mg, preferably about 383 mg, preferably about 384 mg, preferably about 385 mg, preferably about 386 mg, preferably about 387 mg, preferably about 388 mg, preferably about 389 mg, preferably about 390 mg, preferably about 391 mg, preferably about 392 mg, preferably about 393 mg, preferably about 394 mg, preferably about 395 mg, preferably about 396 mg, preferably about 397 mg, preferably about 398 mg, preferably about 399 mg, preferably about 400 mg, preferably about 401 mg, preferably about 402 mg, preferably about 403 mg, preferably about 404 mg, preferably about 405 mg, preferably about 406 mg, preferably about 407 mg, preferably about 408 mg, preferably about 409 mg, preferably about 410 mg, preferably about 411 mg, preferably about 412 mg, preferably about 413 mg, preferably about 414 mg, preferably about 415 mg, preferably about 416 mg, preferably about 417 mg, preferably about 418 mg, preferably about 419 mg, preferably about 420 mg, preferably about 421 mg, preferably about 422 mg, preferably about 423 mg, preferably about 424 mg, preferably about 425 mg, preferably about 426 mg, preferably about 427 mg, preferably about 428 mg, preferably about 429 mg, preferably about 430 mg, preferably about 431 mg, preferably about 432 mg, preferably about 434 mg, preferably about 434 mg, preferably about 435 mg, preferably about 436 mg, preferably about 437 mg, preferably about 438 mg, preferably about 439 mg, preferably about 440 mg, preferably about 441 mg, preferably about 442 mg, preferably about 443 mg, preferably about 444 mg, preferably about 445 mg, preferably about 446 mg, preferably about 447 mg, preferably about 448 mg, preferably about 449 mg, preferably about 450 mg, preferably about 451 mg, preferably about 452 mg, preferably about 453 mg, preferably about 454 mg, preferably about 455 mg, preferably about 456 mg, preferably about 457 mg, preferably about 458 mg, preferably about 459 mg, preferably about 460 mg, preferably about 461 mg, preferably about 462 mg, preferably about 463 mg, preferably about 464 mg, preferably about 465 mg, preferably about 466 mg, preferably about 467 mg, preferably about 468 mg, preferably about 469 mg, preferably about 470 mg, preferably about 471 mg, preferably about 472 mg, preferably about 473 mg, preferably about 474 mg, preferably about 475 mg, preferably about 476 mg, preferably about 477 mg, preferably about 478 mg, preferably about 479 mg, preferably about 480 mg, preferably about 481 mg, preferably about 482 mg, preferably about 483 mg, preferably about 484 mg, preferably about 485 mg, preferably about 486 mg, preferably about 487 mg, preferably about 488 mg, preferably about 489 mg, preferably about 490 mg, preferably about 491 mg, preferably about 492 mg, preferably about 493 mg, preferably about 494 mg, preferably about 495 mg, preferably about 496 mg, preferably about 497 mg, preferably about 498 mg, preferably about 499 mg, preferably about 500 mg, preferably about 501 mg, preferably about 502 mg, preferably about 503 mg, preferably about 504 mg, preferably about 505 mg, preferably about 506 mg, preferably about 507 mg, preferably about 508 mg, preferably about 509 mg, preferably about 510 mg, preferably about 511 mg, preferably about 512 mg, preferably about 513 mg, preferably about 514 mg, preferably about 515 mg, preferably about 516 mg, preferably about 517 mg, preferably about 518 mg, preferably about 519 mg, preferably about 520 mg, preferably about 521 mg, preferably about 522 mg, preferably about 523 mg, preferably about 524 mg, preferably about 525 mg, preferably about 526 mg, preferably about 527 mg, preferably about 528 mg, preferably about 529 mg, preferably about 530 mg, preferably about 531 mg, preferably about 532 mg, preferably about 535 mg, preferably about 534 mg, preferably about 535 mg, preferably about 536 mg, preferably about 537 mg, preferably about 538 mg, preferably about 539 mg, preferably about 540 mg, preferably about 541 mg, preferably about 542 mg, preferably about 543 mg, preferably about 544 mg, preferably about 545 mg, preferably about 546 mg, preferably about 547 mg, preferably about 548 mg, preferably about 549 mg, preferably about 550 mg, preferably about 551 mg, preferably about 552 mg, preferably about 553 mg, preferably about 554 mg, preferably about 555 mg, preferably about 556 mg, preferably about 557 mg, preferably about 558 mg, preferably about 559 mg, preferably about 560 mg, preferably about 561 mg, preferably about 562 mg, preferably about 563 mg, preferably about 564 mg, preferably about 565 mg, preferably about 566 mg, preferably about 567 mg, preferably about 568 mg, preferably about 569 mg, preferably about 570 mg, preferably about 571 mg, preferably about 572 mg, preferably about 573 mg, preferably about 574 mg, preferably about 575 mg, preferably about 576 mg, preferably about 577 mg, preferably about 578 mg, preferably about 579 mg, preferably about 580 mg, preferably about 581 mg, preferably about 582 mg, preferably about 583 mg, preferably about 584 mg, preferably about 585 mg, preferably about 586 mg, preferably about 587 mg, preferably about 588 mg, preferably about 589 mg, preferably about 590 mg, preferably about 591 mg, preferably about 592 mg, preferably about 593 mg, preferably about 594 mg, preferably about 595 mg, preferably about 596 mg, preferably about 597 mg, preferably about 598 mg, preferably about 599 mg, preferably about 600 mg, preferably about 601 mg, preferably about 602 mg, preferably about 603 mg, preferably about 604 mg, preferably about 605 mg, preferably about 606 mg, preferably about 607 mg, preferably about 608 mg, preferably about 609 mg, preferably about 610 mg, preferably about 611 mg, preferably about 612 mg, preferably about 613 mg, preferably about 614 mg, preferably about 615 mg, preferably about 616 mg, preferably about 617 mg, preferably about 618 mg, preferably about 619 mg, preferably about 620 mg, preferably about 621 mg, preferably about 622 mg, preferably about 623 mg, preferably about 624 mg, preferably about 625 mg, preferably about 626 mg, preferably about 627 mg, preferably about 628 mg, preferably about 629 mg, preferably about 630 mg, preferably about 631 mg, preferably about 632 mg, preferably about 636 mg, preferably about 634 mg, preferably about 635 mg, preferably about 636 mg, preferably about 637 mg, preferably about 638 mg, preferably about 639 mg, preferably about 640 mg, preferably about 641 mg, preferably about 642 mg, preferably about 643 mg, preferably about 644 mg, preferably about 645 mg, preferably about 646 mg, preferably about 647 mg, preferably about 648 mg, preferably about 649 mg, preferably about 650 mg, preferably about 651 mg, preferably about 652 mg, preferably about 653 mg, preferably about 654 mg, preferably about 655 mg, preferably about 656 mg, preferably about 657 mg, preferably about 658 mg, preferably about 659 mg, preferably about 660 mg, preferably about 661 mg, preferably about 662 mg, preferably about 663 mg, preferably about 664 mg, preferably about 665 mg, preferably about 666 mg, preferably about 667 mg, preferably about 668 mg, preferably about 669 mg, preferably about 670 mg, preferably about 671 mg, preferably about 672 mg, preferably about 673 mg, preferably about 674 mg, preferably about 675 mg, preferably about 676 mg, preferably about 677 mg, preferably about 678 mg, preferably about 679 mg, preferably about 680 mg, preferably about 681 mg, preferably about 682 mg, preferably about 683 mg, preferably about 684 mg, preferably about 685 mg, preferably about 686 mg, preferably about 687 mg, preferably about 688 mg, preferably about 689 mg, preferably about 690 mg, preferably about 691 mg, preferably about 692 mg, preferably about 693 mg, preferably about 694 mg, preferably about 695 mg, preferably about 696 mg, preferably about 697 mg, preferably about 698 mg, preferably about 699 mg or more preferably about 700 mg.

In an embodiment, the carbonic anhydrase inhibitor or a pharmaceutically acceptable salt thereof is administered at a dose of selected from the group consisting of about 25 mg, about 125 mg, about 250 mg, and about 250 mg.

In an embodiment, the THC or a pharmaceutically acceptable salt thereof is administered at a dose of from about 0.25 mg to about 20 mg (e.g., 0.25 mg, 0.50 mg, 0.75 mg, 1 mg, 1.25 mg, 1.50 mg, 1.75 mg, 2 mg, 2.25 mg, 2.50 mg, 2.75 mg, 3 mg, 3.25 mg, 3.50 mg, 3.75 mg, 4 mg, 4.25 mg, 4.50 mg, 4.75 mg, 5 mg, 5.25 mg, 5.50 mg, 5.75 mg, 6 mg, 6.25 mg, 6.50 mg, 6.75 mg, 7 mg, 7.25 mg, 7.50 mg, 7.75 mg, 8 mg, 8.25 mg, 8.50 mg, 8.75 mg, 9 mg, 9.25 mg, 9.50 mg, 9.75 mg, 10 mg, 10.25 mg, 10.50 mg, 10.75 mg, 11 mg, 11.25 mg, 11.50 mg, 11.75 mg, 12 mg, 12.25 mg, 12.50 mg, 12.75 mg, 13 mg, 13.25 mg, 13.50 mg, 13.75 mg, 14 mg, 14.25 mg, 14.50 mg, 14.75 mg, 15 mg, 15.25 mg, 15.50 mg, 15.75 mg, 16 mg, 16.25 mg, 16.50 mg, 16.75 mg, 17 mg, 17.25 mg, 17.50 mg, 17.75 mg, 18 mg, 18.25 mg, 18.50 mg, 18.75 mg, 19 mg, 19.25 mg, 19.50 mg, 19.75 mg, or 20 mg).

Thus, in an embodiment the THC or a pharmaceutically acceptable salt thereof is administered at a dose of from about 0.25 mg to about 20 mg, preferably about 0.25 mg, preferably about 0.50 mg, preferably about 0.75 mg, preferably about 1 mg, preferably about 1.25 mg, preferably about 1.50 mg, preferably about 1.75 mg, preferably about 2 mg, preferably about 2.25 mg, preferably about 2.50 mg, preferably about 2.75 mg, preferably about 3 mg, preferably about 3.25 mg, preferably about 3.50 mg, preferably about 3.75 mg, preferably about 4 mg, preferably about 4.25 mg, preferably about 4.50 mg, preferably about 4.75 mg, preferably about 5 mg, preferably about 5.25 mg, preferably about 5.50 mg, preferably about 5.75 mg, preferably about 6 mg, preferably about 6.25 mg, preferably about 6.50 mg, preferably about 6.75 mg, preferably about 7 mg, preferably about 7.25 mg, preferably about 7.50 mg, preferably about 7.75 mg, preferably about 8 mg, preferably about 8.25 mg, preferably about 8.50 mg, preferably about 8.75 mg, preferably about 9 mg, preferably about 9.25 mg, preferably about 9.50 mg, preferably about 9.75 mg, preferably about 10 mg, preferably about 10.25 mg, preferably about 10.50 mg, preferably about 10.75 mg, preferably about 11 mg, preferably about 11.25 mg, preferably about 11.50 mg, preferably about 11.75 mg, preferably about 12 mg, preferably about 12.25 mg, preferably about 12.50 mg, preferably about 12.75 mg, preferably about 13 mg, preferably about 13.25 mg, preferably about 13.50 mg, preferably about 13.75 mg, preferably about 14 mg, preferably about 14.25 mg, preferably about 14.50 mg, preferably about 14.75 mg, preferably about 15 mg, preferably about 15.25 mg, preferably about 15.50 mg, preferably about 15.75 mg, preferably about 16 mg, preferably about 16.25 mg, preferably about 16.50 mg, preferably about 16.75 mg, preferably about 17 mg, preferably about 17.25 mg, preferably about 17.50 mg, preferably about 17.75 mg, preferably about 18 mg, preferably about 18.25 mg, preferably about 18.50 mg, preferably about 18.75 mg, preferably about 19 mg, preferably about 19.25 mg, preferably about 19.50 mg, preferably about 19.75 mg, or more preferably about 20 mg.

In an embodiment, the THC or a pharmaceutically acceptable salt thereof is administered at a dose selected from the group consisting of about 0.5 mg, about 2.5 mg, about 5 mg and about 10 mg.

In an embodiment, the THC or a pharmaceutically acceptable salt thereof is administered at a dose of about 0.5 mg, and the carbonic anhydrase inhibitor or a pharmaceutically acceptable salt thereof is administered at a dose of about 25 mg.

In an embodiment, the THC or a pharmaceutically acceptable salt thereof is administered at a dose of about 2.5 mg, and the carbonic anhydrase inhibitor or a pharmaceutically acceptable salt thereof is administered at a dose of about 125 mg.

In an embodiment, the THC or a pharmaceutically acceptable salt thereof is administered at a dose of about 5 mg, and the carbonic anhydrase inhibitor or a pharmaceutically acceptable salt thereof is administered at a dose of about 250 mg.

In an embodiment, the THC or a pharmaceutically acceptable salt thereof is administered at a dose of about 10 mg, and the carbonic anhydrase inhibitor or a pharmaceutically acceptable salt thereof is administered at a dose of about 500 mg.

The THC or a pharmaceutically acceptable salt thereof, and the carbonic anhydrase inhibitor or a pharmaceutically acceptable salt thereof may be administered orally, topically, parenterally, transdermally, by inhalation, intranasally, by irrigation, by implant, by insufflation, topically to the eye, or aurally. The THC or a pharmaceutically acceptable salt thereof, and the carbonic anhydrase inhibitor or a pharmaceutically acceptable salt thereof may be administered in dosage unit and in formulations containing conventional non-toxic pharmaceutically acceptable carriers, adjuvants, and vehicles. Formulations include liposomal, nanoparticle, microparticle, polymer-based, dispersion, suspension, coated on a device, powder, microspheres, carrier-mediated, implant and encapsulation.

The term "parenteral" as used herein includes subcutaneous injections, aerosol for administration to lungs or nasal cavity, intravenous, intramuscular, intrathecal, intracranial, injection or infusion techniques.

Oral administration of THC has been demonstrated to be an efficacious administration route (Goodwin et al., 2006, *Therapeutic Drug Monitoring,* 28(4): 545-551). Similarly, oral administration of carbonic anhydrase inhibitors, such as acetazolamide, have also been demonstrated to be effective for absorption and bioavailability (Wallace et al., 1977, *Journal of Pharmaceutical Sciences,* 66(4): 527-530).

Accordingly, in a preferred embodiment, the THC or a pharmaceutically acceptable salt thereof, and the carbonic anhydrase inhibitor or a pharmaceutically acceptable salt thereof are orally administered to the subject.

Suitable dosage forms for oral administration would be known to persons skilled in the art, illustrative examples of which include tablets, aqueous or oily suspensions, lozenges, troches, powders, granules, emulsions, capsules, liquids, syrups or elixirs.

In an embodiment, the THC or a pharmaceutically acceptable salt thereof, and the carbonic anhydrase inhibitor or a pharmaceutically acceptable salt thereof is in liquid, oil, tablet or capsule form.

Dosage forms for oral administration may comprise one or more agents selected from the group of sweetening agents, flavoring agents, coloring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavoring agents include peppermint oil, oil of wintergreen, cherry, orange or raspberry flavoring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Dosage forms for oral administration may also comprise suitable pharmaceutically acceptable carriers, diluents or excipients known to persons skilled in the art, illustrative examples of which include inert diluents (e.g., calcium carbonate, lactose, calcium phosphate or sodium phosphate), granulating and disintegrating agents (e.g., corn starch or alginic acid), binding agents (e.g., starch, gelatin or acacia), lubricating agents (e.g., magnesium stearate, stearic acid or talc), medium chain triglyceride oil (e.g., sesame oil) and material to delay disintegration and absorption in the gastrointestinal tract and thereby provide a sustained action over a longer period (e.g., glyceryl monostearate or glyceryl distearate, microcrystalline cellulose). Coating may also be performed using techniques described in the U.S. Pat. Nos. 4,256,108, 4,160,452, and 4,265,874 to form osmotic therapeutic tablets for control release.

It is further contemplated herein that the THC or a pharmaceutically acceptable salt thereof, and the carbonic anhydrase inhibitor or a pharmaceutically acceptable salt thereof may be co-administered with one or more other appropriate therapeutic agents, illustrative examples of which include anti-inflammatory agents, bronchodilators and nasal decongestants.

In an aspect disclosed herein, there is provided a use of THC or a pharmaceutically acceptable salt thereof, and a carbonic anhydrase inhibitor or a pharmaceutically acceptable salt thereof, in the manufacture of a medicament for the treatment of OSA.

In another aspect disclosed herein, there is provided THC or a pharmaceutically acceptable salt thereof, and a carbonic anhydrase inhibitor or a pharmaceutically acceptable salt thereof, for use in the treatment of OSA.

In accordance with the methods disclosed herein, the THC or a pharmaceutically acceptable salt thereof, and the carbonic anhydrase inhibitor or a pharmaceutically acceptable salt thereof may be co-administered as separate compositions.

In an embodiment, the THC or a pharmaceutically acceptable salt thereof, and the carbonic anhydrase inhibitor or a pharmaceutically acceptable salt thereof are administered sequentially.

By "sequential" administration it is meant there is an interval between the administration of the THC or a pharmaceutically acceptable salt thereof, and the carbonic anhydrase inhibitor or a pharmaceutically acceptable salt thereof. The interval between sequential administrations may be seconds, minutes, hours or days. In a preferred embodiment, the interval between sequential administrations of the THC or a pharmaceutically acceptable salt thereof, and the carbonic anhydrase inhibitor or a pharmaceutically acceptable salt thereof is less than an hour, preferably less than 30 minutes, most preferably less than 1 minute. Sequential administration may be in any order (i.e., administration of THC or a pharmaceutically acceptable salt thereof prior to the administration of the carbonic anhydrase inhibitor or a pharmaceutically acceptable salt thereof, or administration of the carbonic anhydrase inhibitor or a pharmaceutically acceptable salt thereof prior to the administration of THC or a pharmaceutically acceptable salt thereof).

In another embodiment, the THC or a pharmaceutically acceptable salt thereof, and the carbonic anhydrase inhibitor or a pharmaceutically acceptable salt thereof are administered simultaneously.

By "simultaneous" administration it is meant that the THC or a pharmaceutically acceptable salt thereof, and the carbonic anhydrase inhibitor or a pharmaceutically acceptable salt thereof are administered at the same time. In accordance with the methods disclosed herein, the THC or a pharmaceutically acceptable salt thereof, and the carbonic anhydrase inhibitor or a pharmaceutically acceptable salt thereof may be administered simultaneously as two separate compositions or dosage forms. Alternatively, the THC or acceptable salt thereof, and the carbonic anhydrase inhibitor or a pharmaceutically acceptable salt thereof are administered simultaneously as a single composition or dosage form.

Accordingly, in an embodiment, there is provided a composition comprising Δ-9-tetrahydrocannabinol (THC) or a pharmaceutically acceptable salt thereof, and a carbonic anhydrase inhibitor or a pharmaceutically acceptable salt thereof.

In another embodiment, there is provided a composition comprising Δ-9-tetrahydrocannabinol (THC) or a pharmaceutically acceptable salt thereof, and a carbonic anhydrase inhibitor or a pharmaceutically acceptable salt thereof for use in the treatment of OSA.

In a preferred embodiment, the composition comprising THC or a pharmaceutically acceptable salt thereof, and a carbonic anhydrase inhibitor or a pharmaceutically acceptable salt thereof are formulated for oral administration.

In an embodiment, the composition comprises from about 0.25 mg to about 20 mg THC or a pharmaceutically acceptable salt thereof per dose (e.g., 0.25 mg, 0.50 mg, 0.75 mg, 1 mg, 1.25 mg, 1.50 mg, 1.75 mg, 2 mg, 2.25 mg, 2.50 mg, 2.75 mg, 3 mg, 3.25 mg, 3.50 mg, 3.75 mg, 4 mg, 4.25 mg, 4.50 mg, 4.75 mg, 5 mg, 5.25 mg, 5.50 mg, 5.75 mg, 6 mg, 6.25 mg, 6.50 mg, 6.75 mg, 7 mg, 7.25 mg, 7.50 mg, 7.75 mg, 8 mg, 8.25 mg, 8.50 mg, 8.75 mg, 9 mg, 9.25 mg, 9.50 mg, 9.75 mg, 10 mg, 10.25 mg, 10.50 mg, 10.75 mg, 11 mg, 11.25 mg, 11.50 mg, 11.75 mg, 12 mg, 12.25 mg, 12.50 mg, 12.75 mg, 13 mg, 13.25 mg, 13.50 mg, 13.75 mg, 14 mg, 14.25 mg, 14.50 mg, 14.75 mg, 15 mg, 15.25 mg, 15.50 mg, 15.75 mg, 16 mg, 16.25 mg, 16.50 mg, 16.75 mg, 17 mg, 17.25 mg, 17.50 mg, 17.75 mg, 18 mg, 18.25 mg, 18.50 mg, 18.75 mg, 19 mg, 19.25 mg, 19.50 mg, 19.75 mg, or 20 mg).

Thus, in an embodiment, the composition comprises from about 0.25 mg to about 20 mg THC or a pharmaceutically acceptable salt thereof per dose, preferably about 0.25 mg, preferably about 0.50 mg, preferably about 0.75 mg, preferably about 1 mg, preferably about 1.25 mg, preferably about 1.50 mg, preferably about 1.75 mg, preferably about 2 mg, preferably about 2.25 mg, preferably about 2.50 mg, preferably about 2.75 mg, preferably about 3 mg, preferably about 3.25 mg, preferably about 3.50 mg, preferably about 3.75 mg, preferably about 4 mg, preferably about 4.25 mg, preferably about 4.50 mg, preferably about 4.75 mg, preferably about 5 mg, preferably about 5.25 mg, preferably about 5.50 mg, preferably about 5.75 mg, preferably about 6 mg, preferably about 6.25 mg, preferably about 6.50 mg, preferably about 6.75 mg, preferably about 7 mg, preferably about 7.25 mg, preferably about 7.50 mg, preferably about 7.75 mg, preferably about 8 mg, preferably about 8.25 mg, preferably about 8.50 mg, preferably about 8.75 mg, preferably about 9 mg, preferably about 9.25 mg, preferably about 9.50 mg, preferably about 9.75 mg, preferably about 10 mg, preferably about 10.25 mg, preferably about 10.50 mg, preferably about 10.75 mg, preferably about 11 mg, preferably about 11.25 mg, preferably about 11.50 mg, preferably about 11.75 mg, preferably about 12 mg, preferably about 12.25 mg, preferably about 12.50 mg, preferably about 12.75 mg, preferably about 13 mg, preferably about 13.25 mg, preferably about 13.50 mg, preferably about 13.75 mg, preferably about 14 mg, preferably about 14.25 mg, preferably about 14.50 mg, preferably about 14.75 mg, preferably about 15 mg, preferably about 15.25 mg, preferably about 15.50 mg, preferably about 15.75 mg, preferably about 16 mg, preferably about 16.25 mg, preferably about 16.50 mg, preferably about 16.75 mg, preferably about 17 mg, preferably about 17.25 mg, preferably about 17.50 mg, preferably about 17.75 mg, preferably about 18 mg, preferably about 18.25 mg, preferably about 18.50 mg, preferably about 18.75 mg, preferably about 19 mg, preferably about 19.25 mg, preferably about 19.50 mg, preferably about 19.75 mg, or more preferably about 20 mg.

In an embodiment, the composition comprises from about 1 mg to about 700 mg of the carbonic anhydrase inhibitor or a pharmaceutically acceptable salt thereof per dose (e.g., 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 131 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 434 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, 465 mg, 466 mg, 467 mg, 468 mg, 469 mg, 470 mg, 471 mg, 472 mg, 473 mg, 474 mg, 475 mg, 476 mg, 477 mg, 478 mg, 479 mg, 480 mg, 481 mg, 482 mg, 483 mg, 484 mg, 485 mg, 486 mg, 487 mg, 488 mg, 489 mg, 490 mg, 491 mg, 492 mg, 493 mg, 494 mg, 495 mg, 496 mg, 497 mg, 498 mg, 499 mg, 500 mg, 501 mg, 502 mg, 503 mg, 504 mg, 505 mg, 506 mg, 507 mg, 508 mg, 509 mg, 510 mg, 511 mg, 512 mg, 513 mg, 514 mg, 515 mg, 516 mg, 517 mg, 518 mg, 519 mg, 520 mg, 521 mg, 522 mg, 523 mg, 524 mg, 525 mg, 526 mg, 527 mg, 528 mg, 529 mg, 530 mg, 531 mg, 532 mg, 535 mg, 534 mg, 535 mg, 536 mg, 537 mg, 538 mg, 539 mg, 540 mg, 541 mg, 542 mg, 543 mg, 544 mg, 545 mg, 546 mg, 547 mg, 548 mg, 549 mg, 550 mg, 551 mg, 552 mg, 553 mg, 554 mg, 555 mg, 556 mg, 557 mg, 558 mg, 559 mg, 560 mg, 561 mg, 562 mg, 563 mg, 564 mg, 565 mg, 566 mg, 567 mg, 568 mg, 569 mg, 570 mg, 571 mg, 572 mg, 573 mg, 574 mg, 575 mg, 576 mg, 577 mg, 578 mg, 579 mg, 580 mg, 581 mg, 582 mg, 583 mg, 584 mg, 585 mg, 586 mg, 587 mg, 588 mg, 589 mg, 590 mg, 591 mg, 592 mg, 593 mg, 594 mg, 595 mg, 596 mg, 597 mg, 598 mg, 599 mg, 600 mg, 601 mg, 602 mg, 603 mg, 604 mg, 605 mg, 606 mg, 607 mg, 608 mg, 609 mg, 610 mg, 611 mg, 612 mg, 613 mg, 614 mg, 615 mg, 616 mg, 617 mg, 618 mg, 619 mg, 620 mg, 621 mg, 622 mg, 623 mg, 624 mg, 625 mg, 626 mg, 627 mg, 628 mg, 629 mg, 630 mg, 631 mg, 632 mg, 636 mg, 634 mg, 635 mg, 636 mg, 637 mg, 638 mg, 639 mg, 640 mg, 641 mg, 642 mg, 643 mg, 644 mg, 645 mg, 646 mg, 647 mg, 648 mg, 649 mg, 650 mg, 651 mg, 652 mg, 653 mg, 654 mg, 655 mg, 656 mg, 657 mg, 658 mg, 659 mg, 660 mg, 661 mg, 662 mg, 663 mg, 664 mg, 665 mg, 666 mg, 667 mg, 668 mg, 669 mg, 670 mg, 671 mg, 672 mg, 673 mg, 674 mg, 675 mg, 676 mg, 677 mg, 678 mg, 679 mg, 680 mg, 681 mg, 682 mg, 683 mg, 684 mg, 685 mg, 686 mg, 687 mg, 688 mg, 689 mg, 690 mg, 691 mg, 692 mg, 693 mg, 694 mg, 695 mg, 696 mg, 697 mg, 698 mg, 699 mg or 700 mg)

Thus, in an embodiment, the composition comprises from about 1 mg to about 700 mg of the carbonic anhydrase inhibitor or a pharmaceutically acceptable salt thereof per dose, preferably about 1 mg, preferably about 2 mg, preferably about 3 mg, preferably about 4 mg, preferably about 5 mg, preferably about 6 mg, preferably about 7 mg, preferably about 8 mg, preferably about 9 mg, preferably about 10 mg, preferably about 11 mg, preferably about 12 mg, preferably about 13 mg, preferably about 14 mg, preferably about 15 mg, preferably about 16 mg, preferably about 17 mg, preferably about 18 mg, preferably about 19 mg, preferably about 20 mg, preferably about 21 mg, preferably about 22 mg, preferably about 23 mg, preferably about 24 mg, preferably about 25 mg, preferably about 26 mg, preferably about 27 mg, preferably about 28 mg, preferably about 29 mg, preferably about 30 mg, preferably about 31 mg, preferably about 32 mg, preferably about 33 mg, preferably about 34 mg, preferably about 35 mg, preferably about 36 mg, preferably about 37 mg, preferably about 38 mg, preferably about 39 mg, preferably about 40 mg, preferably about 41 mg, preferably about 42 mg, preferably about 43 mg, preferably about 44 mg, preferably about 45 mg, preferably about 46 mg, preferably about 47 mg, preferably about 48 mg, preferably about 49 mg, preferably about 50 mg, preferably about 51 mg, preferably about 52 mg, preferably about 53 mg, preferably about 54 mg, preferably about 55 mg, preferably about 56 mg, preferably about 57 mg, preferably about 58 mg, preferably about 59 mg, preferably about 60 mg, preferably about 61 mg, preferably about 62 mg, preferably about 63 mg, preferably about 64 mg, preferably about 65 mg, preferably about 66 mg, preferably about 67 mg, preferably about 68 mg, preferably about 69 mg, preferably about 70 mg, preferably about 71 mg, preferably about 72 mg, preferably about 73 mg, preferably about 74 mg, preferably about 75 mg, preferably about 76 mg, preferably about 77 mg, preferably about 78 mg, preferably about 79 mg, preferably about 80 mg, preferably about 81 mg, preferably about 82 mg, preferably about 83 mg, preferably about 84 mg, preferably about 85 mg, preferably about 86 mg, preferably about 87 mg, preferably about 88 mg, preferably about 89 mg, preferably about 90 mg, preferably about 91 mg, preferably about 92 mg, preferably about 93 mg, preferably about 94 mg, preferably about 95 mg, preferably about 96 mg, preferably about 97 mg, preferably about 98 mg, preferably about 99 mg, preferably about 100 mg, preferably about 101 mg, preferably about 102 mg, preferably about 103 mg, preferably about 104 mg, preferably about 105 mg, preferably about 106 mg, preferably about 107 mg, preferably about 108 mg, preferably about 109 mg, preferably about 110 mg, preferably about 111 mg, preferably about 112 mg, preferably about 113 mg, preferably about 114 mg, preferably about 115 mg, preferably about 116 mg, preferably about 117 mg, preferably about 118 mg, preferably about 119 mg, preferably about 120 mg, preferably about 121 mg, preferably about 122 mg, preferably about 123 mg, preferably about 124 mg, preferably about 125 mg, preferably about 126 mg, preferably about 127 mg, preferably about 128 mg, preferably about 129 mg, preferably about 130 mg, preferably about 131 mg, preferably about 132 mg, preferably about 131 mg, preferably about 134 mg, preferably about 135 mg, preferably about 136 mg, preferably about 137 mg, preferably about 138 mg, preferably about 139 mg, preferably about 140 mg, preferably about 141 mg, preferably about 142 mg, preferably about 143 mg, preferably about 144 mg, preferably about 145 mg, preferably about 146 mg, preferably about 147 mg, preferably about 148 mg, preferably about 149 mg, preferably about 150 mg, preferably about 151 mg, preferably about 152 mg, preferably about 153 mg, preferably about 154 mg, preferably about 155 mg, preferably about 156 mg, preferably about 157 mg, preferably about 158 mg, preferably about 159 mg, preferably about 160 mg, preferably about 161 mg, preferably about 162 mg, preferably about 163 mg, preferably about 164 mg, preferably about 165 mg, preferably about 166 mg, preferably about 167 mg, preferably about 168 mg, preferably about 169 mg, preferably about 170 mg, preferably about 171 mg, preferably about 172 mg, preferably about 173 mg, preferably about 174 mg, preferably about 175 mg, preferably about 176 mg, preferably about 177 mg, preferably about 178 mg, preferably about 179 mg, preferably about 180 mg, preferably about 181 mg, preferably about 182 mg, preferably about 183 mg, preferably about 184 mg, preferably about 185 mg, preferably about 186 mg, preferably about 187 mg, preferably about 188 mg, preferably about 189 mg, preferably about 190 mg, preferably about 191 mg, preferably about 192 mg, preferably about 193 mg, preferably about 194 mg, preferably about 195 mg, preferably about 196 mg, preferably about 197 mg, preferably about 198 mg, preferably about 199 mg, preferably about 200 mg, preferably about 201 mg, preferably about 202 mg, preferably about 203 mg, preferably about 204 mg, preferably about 205 mg, preferably about 206 mg, preferably about 207 mg, preferably about 208 mg, preferably about 209 mg, preferably about 210 mg, preferably about 211 mg, preferably about 212 mg, preferably about 213 mg, preferably about 214 mg, preferably about 215 mg, preferably about 216 mg, preferably about 217 mg, preferably about 218 mg, preferably about 219 mg, preferably about 220 mg, preferably about 221 mg, preferably about 222 mg, preferably about 223 mg, preferably about 224 mg, preferably about 225 mg, preferably about 226 mg, preferably about 227 mg, preferably about 228 mg, preferably about 229 mg, preferably about 230 mg, preferably about 231 mg, preferably about 232 mg, preferably about 233 mg, preferably about 234 mg, preferably about 235 mg, preferably about 236 mg, preferably about 237 mg, preferably about 238 mg, preferably about 239 mg, preferably about 240 mg, preferably about 241 mg, preferably about 242 mg, preferably about 243 mg, preferably about 244 mg, preferably about 245 mg, preferably about 246 mg, preferably about 247 mg, preferably about 248 mg, preferably about 249 mg, preferably about 250 mg, preferably about 251 mg, preferably about 252 mg, preferably about 253 mg, preferably about 254 mg, preferably about 255 mg, preferably about 256 mg, preferably about 257 mg, preferably about 258 mg, preferably about 259 mg, preferably about 260 mg, preferably about 261 mg, preferably about 262 mg, preferably about 263 mg, preferably about 264 mg, preferably about 265 mg, preferably about 266 mg, preferably about 267 mg, preferably about 268 mg, preferably about 269 mg, preferably about 270 mg, preferably about 271 mg, preferably about 272 mg, preferably about 273 mg, preferably about 274 mg, preferably about 275 mg, preferably about 276 mg, preferably about 277 mg, preferably about 278 mg, preferably about 279 mg, preferably about 280 mg, preferably about 281 mg, preferably about 282 mg, preferably about 283 mg, preferably about 284 mg, preferably about 285 mg, preferably about 286 mg, preferably about 287 mg, preferably about 288 mg, preferably about 289 mg, preferably about 290 mg, preferably about 291 mg, preferably about 292 mg, preferably about 293 mg, preferably about 294 mg, preferably about 295 mg, preferably about 296 mg, preferably about 297 mg, preferably about 298 mg, preferably about 299 mg, preferably about 300 mg, preferably about 301 mg, preferably about 302 mg, preferably about 303 mg, preferably about 304 mg, preferably about 305 mg, preferably about 306 mg, preferably about 307 mg, preferably about 308 mg, preferably about 309 mg, preferably about 310 mg, preferably about 311 mg, preferably about 312 mg, preferably about 313 mg, preferably about 314 mg, preferably about 315 mg, preferably about 316 mg, preferably about 317 mg, preferably about 318 mg, preferably about 319 mg, preferably about 320 mg, preferably about 321 mg, preferably about 322 mg, preferably about 323 mg, preferably about 324 mg, preferably about 325 mg, preferably about 326 mg, preferably about 327 mg, preferably about 328 mg, preferably about 329 mg, preferably about 330 mg, preferably about 331 mg, preferably about 332 mg, preferably about 333 mg, preferably about 334 mg, preferably about 335 mg, preferably about 336 mg, preferably about 337 mg, preferably about 338 mg, preferably about 339 mg, preferably about 340 mg, preferably about 341 mg, preferably about 342 mg, preferably about 343 mg, preferably about 344 mg, preferably about 345 mg, preferably about 346 mg, preferably about 347 mg, preferably about 348 mg, preferably about 349 mg, preferably about 350 mg, preferably about 351 mg, preferably about 352 mg, preferably about 353 mg, preferably about 354 mg, preferably about 355 mg, preferably about 356 mg, preferably about 357 mg, preferably about 358 mg, preferably about 359 mg, preferably about 360 mg, preferably about 361 mg, preferably about 362 mg, preferably about 363 mg, preferably about 364 mg, preferably about 365 mg, preferably about 366 mg, preferably about 367 mg, preferably about 368 mg, preferably about 369 mg, preferably about 370 mg, preferably about 371 mg, preferably about 372 mg, preferably about 373 mg, preferably about 374 mg, preferably about 375 mg, preferably about 376 mg, preferably about 377 mg, preferably about 378 mg, preferably about 379 mg, preferably about 380 mg, preferably about 381 mg, preferably about 382 mg, preferably about 383 mg, preferably about 384 mg, preferably about 385 mg, preferably about 386 mg, preferably about 387 mg, preferably about 388 mg, preferably about 389 mg, preferably about 390 mg, preferably about 391 mg, preferably about 392 mg, preferably about 393 mg, preferably about 394 mg, preferably about 395 mg, preferably about 396 mg, preferably about 397 mg, preferably about 398 mg, preferably about 399 mg, preferably about 400 mg, preferably about 401 mg, preferably about 402 mg, preferably about 403 mg, preferably about 404 mg, preferably about 405 mg, preferably about 406 mg, preferably about 407 mg, preferably about 408 mg, preferably about 409 mg, preferably about 410 mg, preferably about 411 mg, preferably about 412 mg, preferably about 413 mg, preferably about 414 mg, preferably about 415 mg, preferably about 416 mg, preferably about 417 mg, preferably about 418 mg, preferably about 419 mg, preferably about 420 mg, preferably about 421 mg, preferably about 422 mg, preferably about 423 mg, preferably about 424 mg, preferably about 425 mg, preferably about 426 mg, preferably about 427 mg, preferably about 428 mg, preferably about 429 mg, preferably about 430 mg, preferably about 431 mg, preferably about 432 mg, preferably about 434 mg, preferably about 434 mg, preferably about 435 mg, preferably about 436 mg, preferably about 437 mg, preferably about 438 mg, preferably about 439 mg, preferably about 440 mg, preferably about 441 mg, preferably about 442 mg, preferably about 443 mg, preferably about 444 mg, preferably about 445 mg, preferably about 446 mg, preferably about 447 mg, preferably about 448 mg, preferably about 449 mg, preferably about 450 mg, preferably about 451 mg, preferably about 452 mg, preferably about 453 mg, preferably about 454 mg, preferably about 455 mg, preferably about 456 mg, preferably about 457 mg, preferably about 458 mg, preferably about 459 mg, preferably about 460 mg, preferably about 461 mg, preferably about 462 mg, preferably about 463 mg, preferably about 464 mg, preferably about 465 mg, preferably about 466 mg, preferably about 467 mg, preferably about 468 mg, preferably about 469 mg, preferably about 470 mg, preferably about 471 mg, preferably about 472 mg, preferably about 473 mg, preferably about 474 mg, preferably about 475 mg, preferably about 476 mg, preferably about 477 mg, preferably about 478 mg, preferably about 479 mg, preferably about 480 mg, preferably about 481 mg, preferably about 482 mg, preferably about 483 mg, preferably about 484 mg, preferably about 485 mg, preferably about 486 mg, preferably about 487 mg, preferably about 488 mg, preferably about 489 mg, preferably about 490 mg, preferably about 491 mg, preferably about 492 mg, preferably about 493 mg, preferably about 494 mg, preferably about 495 mg, preferably about 496 mg, preferably about 497 mg, preferably about 498 mg, preferably about 499 mg, preferably about 500 mg, preferably about 501 mg, preferably about 502 mg, preferably about 503 mg, preferably about 504 mg, preferably about 505 mg, preferably about 506 mg, preferably about 507 mg, preferably about 508 mg, preferably about 509 mg, preferably about 510 mg, preferably about 511 mg, preferably about 512 mg, preferably about 513 mg, preferably about 514 mg, preferably about 515 mg, preferably about 516 mg, preferably about 517 mg, preferably about 518 mg, preferably about 519 mg, preferably about 520 mg, preferably about 521 mg, preferably about 522 mg, preferably about 523 mg, preferably about 524 mg, preferably about 525 mg, preferably about 526 mg, preferably about 527 mg, preferably about 528 mg, preferably about 529 mg, preferably about 530 mg, preferably about 531 mg, preferably about 532 mg, preferably about 535 mg, preferably about 534 mg, preferably about 535 mg, preferably about 536 mg, preferably about 537 mg, preferably about 538 mg, preferably about 539 mg, preferably about 540 mg, preferably about 541 mg, preferably about 542 mg, preferably about 543 mg, preferably about 544 mg, preferably about 545 mg, preferably about 546 mg, preferably about 547 mg, preferably about 548 mg, preferably about 549 mg, preferably about 550 mg, preferably about 551 mg, preferably about 552 mg, preferably about 553 mg, preferably about 554 mg, preferably about 555 mg, preferably about 556 mg, preferably about 557 mg, preferably about 558 mg, preferably about 559 mg, preferably about 560 mg, preferably about 561 mg, preferably about 562 mg, preferably about 563 mg, preferably about 564 mg, preferably about 565 mg, preferably about 566 mg, preferably about 567 mg, preferably about 568 mg, preferably about 569 mg, preferably about 570 mg, preferably about 571 mg, preferably about 572 mg, preferably about 573 mg, preferably about 574 mg, preferably about 575 mg, preferably about 576 mg, preferably about 577 mg, preferably about 578 mg, preferably about 579 mg, preferably about 580 mg, preferably about 581 mg, preferably about 582 mg, preferably about 583 mg, preferably about 584 mg, preferably about 585 mg, preferably about 586 mg, preferably about 587 mg, preferably about 588 mg, preferably about 589 mg, preferably about 590 mg, preferably about 591 mg, preferably about 592 mg, preferably about 593 mg, preferably about 594 mg, preferably about 595 mg, preferably about 596 mg, preferably about 597 mg, preferably about 598 mg, preferably about 599 mg, preferably about 600 mg, preferably about 601 mg, preferably about 602 mg, preferably about 603 mg, preferably about 604 mg, preferably about 605 mg, preferably about 606 mg, preferably about 607 mg, preferably about 608 mg, preferably about 609 mg, preferably about 610 mg, preferably about 611 mg, preferably about 612 mg, preferably about 613 mg, preferably about 614 mg, preferably about 615 mg, preferably about 616 mg, preferably about 617 mg, preferably about 618 mg, preferably about 619 mg, preferably about 620 mg, preferably about 621 mg, preferably about 622 mg, preferably about 623 mg, preferably about 624 mg, preferably about 625 mg, preferably about 626 mg, preferably about 627 mg, preferably about 628 mg, preferably about 629 mg, preferably about 630 mg, preferably about 631 mg, preferably about 632 mg, preferably about 636 mg, preferably about 634 mg, preferably about 635 mg, preferably about 636 mg, preferably about 637 mg, preferably about 638 mg, preferably about 639 mg, preferably about 640 mg, preferably about 641 mg, preferably about 642 mg, preferably about 643 mg, preferably about 644 mg, preferably about 645 mg, preferably about 646 mg, preferably about 647 mg, preferably about 648 mg, preferably about 649 mg, preferably about 650 mg, preferably about 651 mg, preferably about 652 mg, preferably about 653 mg, preferably about 654 mg, preferably about 655 mg, preferably about 656 mg, preferably about 657 mg, preferably about 658 mg, preferably about 659 mg, preferably about 660 mg, preferably about 661 mg, preferably about 662 mg, preferably about 663 mg, preferably about 664 mg, preferably about 665 mg, preferably about 666 mg, preferably about 667 mg, preferably about 668 mg, preferably about 669 mg, preferably about 670 mg, preferably about 671 mg, preferably about 672 mg, preferably about 673 mg, preferably about 674 mg, preferably about 675 mg, preferably about 676 mg, preferably about 677 mg, preferably about 678 mg, preferably about 679 mg, preferably about 680 mg, preferably about 681 mg, preferably about 682 mg, preferably about 683 mg, preferably about 684 mg, preferably about 685 mg, preferably about 686 mg, preferably about 687 mg, preferably about 688 mg, preferably about 689 mg, preferably about 690 mg, preferably about 691 mg, preferably about 692 mg, preferably about 693 mg, preferably about 694 mg, preferably about 695 mg, preferably about 696 mg, preferably about 697 mg, preferably about 698 mg, preferably about 699 mg or more preferably about 700 mg.

In some embodiments, periodic re-administration of the active agents (either sequentially or simultaneously) may be required to achieve a desirable therapeutic effect. The exact amounts and rates of administration of the THC or a pharmaceutically acceptable salt thereof, and the carbonic anhydrase inhibitor or a pharmaceutically acceptable salt thereof will depend on a number of factors, examples of which are described elsewhere herein, such as the subject's age, body weight, general health, sex and dietary requirements, as well as any drugs or agents used in combination or coincidental with the administration of the composition. Where multiple divided doses are required, these may be administered hourly, daily, weekly, monthly or at other suitable time intervals or the dose may be proportionally reduced as indicated by the exigencies of the situation.

In an embodiment, the THC or a pharmaceutically acceptable salt thereof, and the carbonic anhydrase inhibitor or a pharmaceutically acceptable salt thereof are administered daily.

In an embodiment, the THC or a pharmaceutically acceptable salt thereof, and the carbonic anhydrase inhibitor or a pharmaceutically acceptable salt thereof are administered between 1 to 2 times per day.

In an embodiment, the THC or a pharmaceutically acceptable salt thereof, and the carbonic anhydrase inhibitor or a pharmaceutically acceptable salt thereof are administered 2 times per day.

In an embodiment, the THC or a pharmaceutically acceptable salt thereof and the carbonic anhydrase inhibitor or a pharmaceutically acceptable salt thereof are administered to the subject between about 10 minutes and about 120 minutes before sleep (e.g., 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, 60 minutes, 61 minutes, 62 minutes, 63 minutes, 64 minutes, 65 minutes, 66 minutes, 67 minutes, 68 minutes, 69 minutes, 70 minutes, 71 minutes, 72 minutes, 73 minutes, 74 minutes, 75 minutes, 76 minutes, 77 minutes, 78 minutes, 79 minutes, 80 minutes, 81 minutes, 82 minutes, 83 minutes, 84 minutes, 85 minutes, 86 minutes, 87 minutes, 88 minutes, 89 minutes, 90 minutes, 91 minutes, 92 minutes, 93 minutes, 94 minutes, 95 minutes, 96 minutes, 97 minutes, 98 minutes, 99 minutes, 100 minutes, 101 minutes, 102 minutes, 103 minutes, 104 minutes, 105 minutes, 106 minutes, 107 minutes, 108 minutes, 109 minutes, 110 minutes, 111 minutes, 112 minutes, 113 minutes, 114 minutes, 115 minutes, 116 minutes, 117 minutes, 118 minutes, 119 minutes, or 120 minutes before sleep).

Thus, in an embodiment the THC or a pharmaceutically acceptable salt thereof, and the carbonic anhydrase inhibitor or a pharmaceutically acceptable salt thereof are administered to the subject between about 10 minutes and about 120 minutes before sleep, preferably about 10 minutes, preferably about 11 minutes, preferably about 12 minutes, preferably about 13 minutes, preferably about 14 minutes, preferably about 15 minutes, preferably about 16 minutes, preferably about 17 minutes, preferably about 18 minutes, preferably about 19 minutes, preferably about 20 minutes, preferably about 21 minutes, preferably about 22 minutes, preferably about 23 minutes, preferably about 24 minutes, preferably about 25 minutes, preferably about 26 minutes, preferably about 27 minutes, preferably about 28 minutes, preferably about 29 minutes, preferably about 30 minutes, preferably about 31 minutes, preferably about 32 minutes, preferably about 33 minutes, preferably about 34 minutes, preferably about 35 minutes, preferably about 36 minutes, preferably about 37 minutes, preferably about 38 minutes, preferably about 39 minutes, preferably about 40 minutes, preferably about 41 minutes, preferably about 42 minutes, preferably about 43 minutes, preferably about 44 minutes, preferably about 45 minutes, preferably about 46 minutes, preferably about 47 minutes, preferably about 48 minutes, preferably about 49 minutes, preferably about 50 minutes, preferably about 51 minutes, preferably about 52 minutes, preferably about 53 minutes, preferably about 54 minutes, preferably about 55 minutes, preferably about 56 minutes, preferably about 57 minutes, preferably about 58 minutes, preferably about 59 minutes, preferably about 60 minutes, preferably about 61 minutes, preferably about 62 minutes, preferably about 63 minutes, preferably about 64 minutes, preferably about 65 minutes, preferably about 66 minutes, preferably about 67 minutes, preferably about 68 minutes, preferably about 69 minutes, preferably about 70 minutes, preferably about 71 minutes, preferably about 72 minutes, preferably about 73 minutes, preferably about 74 minutes, preferably about 75 minutes, preferably about 76 minutes, preferably about 77 minutes, preferably about 78 minutes, preferably about 79 minutes, preferably about 80 minutes, preferably about 81 minutes, preferably about 82 minutes, preferably about 83 minutes, preferably about 84 minutes, preferably about 85 minutes, preferably about 86 minutes, preferably about 87 minutes, preferably about 88 minutes, preferably about 89 minutes, preferably about 90 minutes, preferably about 91 minutes, preferably about 92 minutes, preferably about 93 minutes, preferably about 94 minutes, preferably about 95 minutes, preferably about 96 minutes, preferably about 97 minutes, preferably about 98 minutes, preferably about 99 minutes, preferably about 100 minutes, preferably about 101 minutes, preferably about 102 minutes, preferably about 103 minutes, preferably about 104 minutes, preferably about 105 minutes, preferably about 106 minutes, preferably about 107 minutes, preferably about 108 minutes, preferably about 109 minutes, preferably about 110 minutes, preferably about 111 minutes, preferably about 112 minutes, preferably about 113 minutes, preferably about 114 minutes, preferably about 115 minutes, preferably about 116 minutes, preferably about 117 minutes, preferably about 118 minutes, preferably about 119 minutes, or more preferably about 120 minutes before sleep.

In another embodiment, the THC or a pharmaceutically acceptable salt thereof, and the carbonic anhydrase inhibitor or a pharmaceutically acceptable salt thereof are administered to the subject between about 30 minutes and about 60 minutes before sleep.

In other embodiments disclosed herein, the THC or a pharmaceutically acceptable salt thereof, and the carbonic anhydrase inhibitor or a pharmaceutically acceptable salt thereof are formulated as separate unit dosage forms for administration. The unit dosage form may be suitable for oral administration, e.g., solution, capsule or tablet form. Those skilled in the art will appreciate that unit dosage forms comprising THC or a pharmaceutically acceptable salt thereof and/or the carbonic anhydrase inhibitor or a pharmaceutically acceptable salt thereof need not be of the same type. Thus, methods of the present disclosure contemplate the administration of, for example, THC by oil and the carbonic anhydrase inhibitor by a capsule or tablet.

The present inventors will demonstrate that intervention by administration of the active agents (i.e., THC or a pharmaceutically acceptable salt thereof, and an carbonic anhydrase inhibitor or a pharmaceutically acceptable salt thereof) can treat OSA (e.g., by reducing or alleviating symptoms or severity of OSA, in particular, sleep-related respiratory events including apnoeas, hypopnoeas and respiratory event-related arousals). It is expected that oral administration will enable the active agents to cross the blood-brain barrier to affect the therapeutic outcomes described herein.

Kits

The present disclosure further contemplates a kit comprising THC or a pharmaceutically acceptable salt thereof, and a carbonic anhydrase inhibitor or a pharmaceutically acceptable salt thereof for use in the treatment of OSA.

All essential materials and reagents required for treating OSA in a subject may be assembled together in a kit. In an embodiment, the kit comprises two separate pharmaceutical compositions: one containing the THC or a pharmaceutically acceptable salt thereof and the second containing the carbonic anhydrase inhibitor or a pharmaceutically acceptable salt thereof. In another embodiment, the kit comprises a containing or containing the separate compositions such as a divided bottle or a divided foil packet. Additional examples of suitable containers include syringes (e.g., pre-filled syringes), boxes and bags. Typically, the kit further comprises directions for the use of the components.

In an embodiment, the kit comprises the THC or a pharmaceutically acceptable salt thereof and the carbonic anhydrase inhibitor or a pharmaceutically acceptable salt thereof in a blister pack. The term "blister pack" as used herein refers to a commonly used packaging of pharmaceutical unit dosage forms (e.g., tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. The tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

In an embodiment, the kit further comprises a memory aid, e.g., in the form of numbers or a code next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent to persons skilled in the art.

The kit may also optionally include appropriate therapeutic agents to be administered in combination with the THC or a pharmaceutically acceptable salt thereof and the carbonic anhydrase inhibitor or a pharmaceutically acceptable salt thereof, illustrative examples of which include anti-inflammatory agents, bronchodilators and nasal decongestants.

The present disclosure also contemplates a commercial package, also referred to as a "treatment pack" comprising the THC or a pharmaceutically acceptable salt thereof, and the carbonic anhydrase inhibitor or a pharmaceutically acceptable salt thereof, together with instructions for use for the treatment of OSA.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Unless otherwise defined, all technical and scientific terms used herein have the same meanings as commonly understood by one of ordinary skill in the art to which this invention belongs.

All patents, patent applications and publications mentioned herein are hereby incorporated by reference in their entireties.

The various embodiments enabled herein are further described by the following non-limiting examples.

EXAMPLES

Example 1—Exemplary Combinations for the Treatment of Obstructive Sleep Apnoea (OSA)

Exemplary combinations according to the present disclosure have the following ingredients:

TABLE 3

Exemplary combinations

| Combination | Dose (mg) Dronabinol | Acetazolamide |
|---|---|---|
| 1 (low dose) | 0.5 | 25 |
| 2 (medium dose A) | 2.5 | 125 |
| 3 (medium dose B) | 5 | 250 |
| 4 (high dose) | 10 | 500 |

Example 2—Exemplary Methods for the Treatment of Respiratory Symptoms of OSA An exemplary method for the treatment of OSA according to the present disclosure is as follows:

Combination of Example 1: oral administration or co-administration of active agents to the subject nightly (i.e., between 10 to 60 minutes before sleep).

Example 3—Clinical Trial Design and Plan

Twelve subjects with known or suspected OSA (i.e., Apnoea-Hypopnoea Index (AHI)≥15) are to be randomized three-way crossover design with placebo run-in, to investigate the effects of the combination of Δ-9-tetrahydrocannabinol (THC) or a pharmaceutically acceptable salt thereof (i.e., dronabinol) and a carbonic anhydrase inhibitor or a pharmaceutically acceptable salt thereof (i.e., acetazolamide) at three different dose levels on AHI, oxygen desaturation index (ODI), daytime somnolence, and subject well-being. The total treatment time for subjects is 56 days, including 28 treatment days and 28 washout days.

Subjects are to complete five sleep studies (V1-V5) at a sleep clinic that will involve overnight monitoring of subjects using overnight polysomnogram (PSG). At each sleep clinic visit, subjects are to complete a series of questionnaires, including Epworth Sleepiness Scale, SF-36 and POMS, to assess daytime somnolence, mood and quality of life. A blood sample will also be collected to assess blood cell count, electrolytes, urea, liver enzymes and levels of THC and the two main metabolites of THC, being OH-THC and COOH-THC.

The first sleep study (V1) will be used to confirm OSA in the subject and to establish baseline AHI. Thereafter, subjects will be provided with treatment packs for the subsequent treatment periods, with each treatment pack comprising doses numbered with the treatment week (i.e., 1-4) and the treatment night (i.e., 1-7). All treatment packs will contain placebo during week 1. Subjects will be randomized into one of six treatment arms, where the order of low, medium and high dose treatment periods will be different in each of the six treatment arms (Table 4).

TABLE 4

Treatment period randomization

| Arm | Treatment Periods |
|---|---|
| 1 | Placebo-Low-Medium(A/B)-High |
| 2 | Placebo-Low-High-Medium(A/B) |
| 3 | Placebo-Medium(A/B)-Low-High |
| 4 | Placebo-Medium(A/B)-High-Low |
| 5 | Placebo-High-Low-Medium(A/B) |
| 6 | Placebo-High-Medium(A/B)- Low |
| 7 | Placebo-Medium(A) |
| 8 | Placebo-Medium(B) |

All treatment periods will be followed by a seven night washout period. Accordingly, the second sleep study (V2) will occur on night seven of treatment period 1 (i.e., placebo), the third sleep study (V3) will occur on night seven of treatment period 2, the fourth sleep study (V4) will occur on night seven of treatment period 3 and the fifth sleep study (V5) will occur on night seven of treatment period 4 (Table 5). Approximately ten days after the fifth sleep study (V5), subjects will return to the sleep clinic for an end of study visit (V6) where adverse events will be reported, ESS, POMS and SF-36 questionnaires will be completed, and a final blood sample will be collected.

TABLE 5

Treatment schedule including washout periods

| Period | Study Days | Dose | Route and Time |
|---|---|---|---|
| T1 | 1-7 | 1 × placebo capsule A<br>1 × placebo capsule D | Taken orally one hour before bed every night |
| W1 | 8-14 | Washout | |
| T2 | 15-21 | 1 × capsule A<br>1 × capsule D | Taken orally one hour before bed every night |
| W2 | 22-28 | Washout | |
| T3 | 29-35 | 1 × capsule A<br>1 × capsule D | Taken orally one hour before bed every night |
| W3 | 36-42 | Washout | |
| T4 | 43-49 | 1 × capsule A<br>1 × capsule D | Taken orally one hour before bed every night |
| W4 | 50-60 | Washout | |

Efficacy of each trial group is assessed based on the results of the overnight PGS and from the sleep quality/length/well-being measures as compared using a mixed design analysis of covariance (MANCOVA), with treatment (placebo, low, medium, high dose) as the between-subject variable, time as the within-subjects variable, and baseline score as the covariate.

Dronabinol is highly lipid-soluble and will typically achieve significant concentrations in plasma/blood within 30-60 minutes of ingestion, with peak effects within 2-4 hours of ingestion. Acetazolamide is fairly rapidly absorbed from the gastro-intestinal tract and will typically achieve mean peak plasma concentrations within about 2 hours of ingestion.

OSA can negatively affect physical and psychological functioning, as well as quality of life. Sleep disruption and blood gas abnormalities prevent sleep-related restorative processes, and further induce chemical and structural central nervous system cellular injury. This, in turn, leads to dysfunction of prefrontal regions of the brain cortex, manifested behaviorally in what neuropsychologists have termed "executive dysfunction". Executive dysfunction is proposed to markedly affect the functional application of cognitive abilities, resulting in maladaptive daytime behaviors. Reduced alertness, slowed reaction times and poorer concentration lead to increased risk for accidents involving motor vehicles and operating machinery.

It is expected that the nightly administration of THC and a carbonic anhydrase inhibitor will stabilize the respiratory patterns of patients with OSA to effectively manage sleep-related respiratory events and normalize the AHI and oxyhemoglobin saturation levels to improve neurocognitive deficits and associated symptoms. Without being bound by theory or by a particular mode of application, the alteration in vagal balance associated with THC (e.g., dronabinol) likely synergizes with the metabolic acidosis induced by the carbonic anhydrase inhibitor (e.g., acetazolamide), which in turn increases the different between the prevailing partial pressure of $CO_2$ and the apneic threshold partial pressure of $CO_2$ to treat OSA. The co-administration of THC and the carbonic anhydrase inhibitor should enable the reduction in the concentration of the effective amount for both agents to safe, non-toxic levels, while still achieving clinical efficacy.

Example 4—Clinical Trial Results

Subject 1 completed treatment period 7 and Subject 2 completed treatment period 8 as detailed in Table 4, above. On night seven of each treatment period the subjects underwent overnight polysomnography to determine their AHI, as described elsewhere herein. The AHI data and reduction relative to baseline for each subject is shown in Table 6.

TABLE 6

| AHI following combination therapy of dronabinol and acetazolamide according to Medium Dose A and Medium Dose B treatment periods | | |
|---|---|---|
| | 2.5 mg dronabinol + 125 mg acetazolamide (Subject 1) | 5 mg dronabinol + 250 mg acetazolamide (Subject 2) |
| AHI baseline | 28.3 | 31 |
| AHI placebo | 31.0 | 23.4 |
| AHI post-treatment | 4.9 | 10.3 |
| AHI reduction relative to baseline (%) | 82.7 | 66.8 |

These data demonstrate that the combination of dronabinol and acetazolamide are highly effective for the treatment of OSA, particularly as the AHI measured for each patient indicates a reduction in the staging of OSA from severe/moderate to none or mild (Table 1).

In view of the unexpectedly efficacious combination of dronabinol and acetazolamide for the treatment of OSA, published results of the effect of dronabinol and acetazolamide as single agents for the treatment of OSA were used to determine if the combination of dronabinol and acetazolamide was synergistic. Thirteen published studies report on the effect of acetazolamide as a single agent for the treatment of OSA. These studies tested a range of doses across a selection of different patient cohorts. The reduction in AHI observed was from 19.8% to 60.2%. To determine the dose-response relationship between acetazolamide and AHI reduction as relevant to the current study, the published study designs were assessed for agreement with the inclusion/exclusion criteria applied for this study. Studies that included subjects with congestive heart failure, performed at altitude, variable dosing or low baseline AHI (<15) were excluded from further analysis, which resulted in seven studies for inclusion in the analysis described herein (Table 7). The acetazolamide dose and reduction in AHI relative to baseline or placebo were graphically represented and a linear trend line plotted to estimate the relationship between AHI reduction and acetazolamide dose (FIG. 1). There was a strong correlation between acetazolamide dose and AHI reduction ($R^2$=0.9276). The linear trend line was used to predict the AHI reduction for the acetazolamide doses used in the present study (Table 8).

TABLE 7

Published studies on the effect of acetazolamide on AHI in subjects with OSA

| Acetazolamide dose/day (mg) | Baseline/placebo AHI | Acetazolamide AHI | Reduction in AHI (%) | Reference |
|---|---|---|---|---|
| 375 | 26.9 | 17.3 | 35.7 | Inoue, 1987 |
| 1000 | 50 | 26 | 48 | Whyte, 1988 |
| 250 | 25 | 18.1 | 27.6 | Tojima, 1988 |
| 250 | 38.9 | 29.6 | 23.9 | Chin, 1992 |
| 351.2 | 27.1 | 19.1 | 29.5 | Inoue, 1999 |
| 750 | 38 | 23 | 39.5 | Eskandari, 2018 |
| 1000 | 49.6 | 24 | 51.6 | Edwards, 2012 |

TABLE 8

Predicted AHI reduction for single agent acetazolamide treatment of OSA

| Acetazolamide dose (mg) | AHI reduction (%) |
|---|---|
| 125 | 23.4 |
| 250 | 27.1 |
| 500 | 34.5 |

Figure 2:
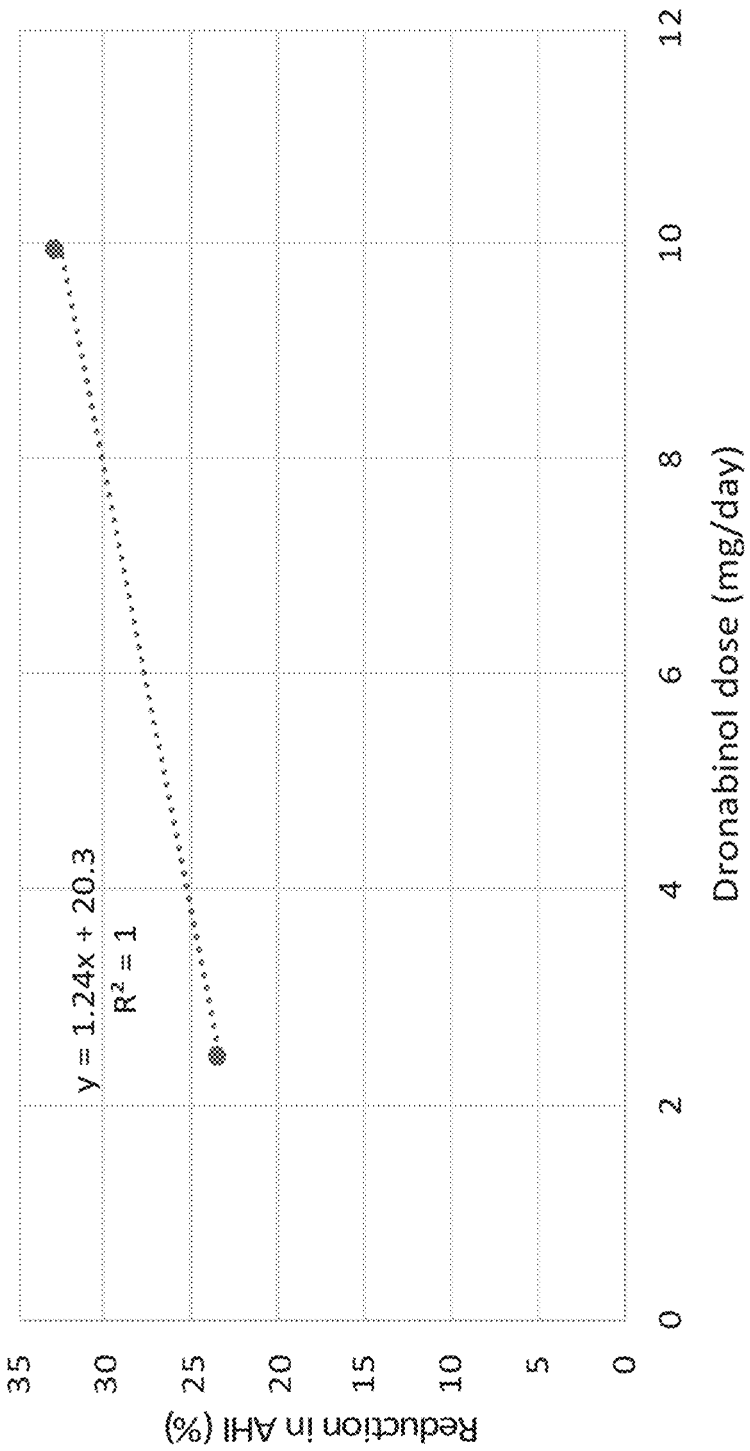
FIG. 2 is a graphical representation of dose response to dronabinol (mg/day; x-axis) and reduction in AHI relative to baseline or placebo (%; y-axis).

A similar analysis was undertaken for dronabinol using the data from Carley et al. (2018, *Sleep,* 41(1): zsx184). The dose-response relationship for two doses of dronabinol (i.e., 2.5 mg and 10 mg) was determined using the method described above in relation to acetazolamide (Table 9; FIG. 2). The resulting trend line was used to determine the predicted reduction in AHI at the doses used in this study (Table 10).

TABLE 9

Published study on the effect of dronabinol on AHI in subjects with OSA

| Dronabinol dose/day (mg) | Baseline AHI | Dronabinol AHI | Reduction in AHI compared to baseline (%) |
|---|---|---|---|
| 10 | 26 | 17.5 | 32.7 |
| 2.5 | 28.2 | 21.6 | 23.4 |

TABLE 10

Predicted AHI reduction for single agent dronabinol treatment of OSA

| Dronabinol dose/day (mg) | AHI reduction (%) |
|---|---|
| 2.5 | 23.4 |
| 5 | 26.5 |
| 10 | 32.7 |

The predicted combinatorial effect of the combination of dronabinol and acetazolamide at the doses used in the present study was calculated using the Bliss Independence Method using the equation $E_{pred\ A+B}=(E_A+E_B)-(E_AE_B)$ The results are shown in Table 11. Synergy between two agents occurs when the difference between the observed activity of agents in combination is greater than the predicted activity. Based on these measures, the combination of dronabinol and acetazolamide synergize to reduce AHI in patients with OSA (Table 12).

TABLE 11

| Predicted AHI reduction for dronabinol and acetazolamide combination therapy as compared to actual clinical results | |
|---|---|
| Dose/day (mg) | Predicted reduction in AHI (%) |
| 125 acetazolmaide<br>2.5 dronabinol | 41.3 |
| 250 acetazolamide<br>5 dronabinol | 46.4 |
| 500 acetazolamide<br>10 dronabinol | 56.0 |

TABLE 12

| Analysis of synergistic effect of dronabinol and acetazolamide combination therapy for the treatment of OSA | | |
|---|---|---|
| | 2.5 mg dronabinol + 125 mg acetazolamide (Subject 1) | 5 mg dronabinol + 250 mg acetazolamide (Subject 2) |
| Predicted combination effect (AHI reduction relative to baseline; %) | 41.3 | 46.4 |
| Observed combination effect (AHI reduction relative to baseline; %) | 82.7 | 66.8 |
| Observed - predicted effect (%) | 41.4 | 20.4 |

CONCLUSION

The data presented herein demonstrate that the combination of THC and a carbonic anhydrase inhibitor, e.g., acetazolamide, unexpectedly synergize to treat OSA. The co-administration of two different doses of both THC and a carbonic anhydrase inhibitor is sufficient to reduce AHI, which is an accepted clinical measure for the treatment and/or amelioration of symptoms associated with OSA. Taken together, these data are enabling for method for the treatment of OSA, and compositions for simultaneous administration of THC and a carbonic anhydrase inhibitor whether in a single composition or dosage form, or co-administration of two separate compositions or dosage forms.

BIBLIOGRAPHY

Benjafiled et al., 2018, *Risk and Prevalence of Sleep Disordered Breathing*: A3962-A3962
Buysse et al., 1989, *Psychiatry Research,* 28(2): 193-213
Carley et al., 2018, *Sleep,* 41(1): zsx184
Chin et al., 1992, *Japanese Journal of Thoracic Disease,* 30:270-277
de Souse Michels et al., 2014, *International Journal of Otolaryngology,* 2014: 717419
Drager et al., 2017, *Circulation,* 136(19): 1840-1850
Edwards et al., 2012, *The Journal of Physiology,* 590:1199-1211
Eubanks et al., 2006, *Molecular Pharmaceuticals,* 3(6): 773-7
Eskandari et al., 2018, *Journal of Clinical Sleep Medicine,* 14:309-317.
Goodwin et al., 2006, *Therapeutic Drug Monitoring,* 28(4): 545-551
Grote, 2019, *The Lancet Respiratory Medicine,* 7(8): 645-647
Iber et al., 2007, *The AASM Manual for the Scoring of Sleep and Associated Events,* 1st edition
Inoue, 1987, *Japanese Journal of Neuropsychopharmacology,* 9:493-513
Inoue et al., 1999, *Psychiatry and Clinical Neurosciences,* 53:321-322.
Johns, 1991, *Sleep,* 14: 540-545
Kogan et al., 2016, *Respiratory Care,* 61(8): 1033-1037
McNair et al., 1971, *POMS Manual for the Profile of Mood States*, San Diego, CA: Educational and Industrial Testing Service
Olaithe et al., 2018, *Sleep Medicine Reviews,* 38: 39-49
Roche et al., 2003, *European Respiratory Journal,* 22: 937-942
Saris-Baglama et al., 2010, *QualityMetric Health Outcomes Scoring Software* 4.0, Lincoln, RI
Shahid et al., 2011, *Leeds Sleep Evaluation Questionnaire* (*LSEQ*), in Shahid et al. (eds), STOP, THAT and One Hundred Other Sleep Scales, Springer, New York
Stoohs et al., 1994, *Sleep,* 17(7): 619-623
Swenson, 2014, *Carbonic Anhydrase Inhibitors and High Altitude Illness*, in: Frost and McKenna (eds), *Carbonic Anhydrase: Mechanism, Regulation, Links to Disease, and Industrial Applications. Subcellular Biochemistry*, vol. 75, Springer, Dordrecht
Tojima et al., 1988, *Thorax,* 43:113-119
Wallace et al., 1977, *Journal of Pharmaceutical Sciences,* 66(4): 527-530
Wheaton et al., 2012, *Sleep,* 35(4): 461-467
Whyte et al., 1988, *Sleep,* 11:463-472
Zamarron et al., 2003, *Chest,* 123(5): 1567-1576
U.S. patent application Ser. No. 11/840,585
U.S. Pat. No. 4,160,452
U.S. Pat. No. 4,256,108
U.S. Pat. No. 4,265,874
U.S. Pat. No. 5,227,537
U.S. Pat. No. 7,323,576
U.S. Pat. No. 10,189,762
WO 2004/016277

The invention claimed is:

1. A method for the treatment of obstructive sleep apnoea (OSA), the method comprising administering to a subject in need thereof Δ-9-tetrahydrocannabinol (THC) or a pharmaceutically acceptable salt thereof, and acetazolamide or a pharmaceutically acceptable salt thereof.

2. The method of claim 1, wherein the acetazolamide is administered at a dose of from about 1 mg to about 700 mg.

3. The method of claim 2, wherein the acetazolamide is administered at a dose selected from the group consisting of about 25 mg, about 125 mg, about 250 mg, and about 500 mg.

4. The method of claim 1, wherein the THC is synthetic THC.

5. The method of claim 1, wherein the THC is administered at a dose of from about 0.25 mg to about 20 mg.

6. The method of claim 5, wherein the THC is administered at a dose selected from the group consisting of about 0.5 mg, about 2.5 mg, about 5 mg, and about 10 mg.

7. The method of claim 1, wherein the THC and the acetazolamide are orally administered to the subject.

8. The method of claim 1, wherein the OSA is mild to severe OSA according to the Apnoea-Hypopnoea Index (AHI).

9. The method of claim 1, wherein the OSA is moderate to severe OSA according to the AHI.

10. The method of claim 1, wherein the THC and the acetazolamide are administered to the subject from about 10 minutes to about 60 minutes prior to sleep.

11. The method of claim 10, wherein the THC and the acetazolamide are administered to the subject from about 30 minutes to about 60 minutes prior to sleep.

12. The method of claim 1, wherein the THC and the acetazolamide are sequentially administered.

13. The method of claim 1, wherein the THC and acetazolamide are simultaneously administered.

14. A kit comprising Δ-9-tetrahydrocannabinol (THC) or a pharmaceutically acceptable salt thereof, and acetazolamide or a pharmaceutically acceptable salt thereof for use in the treatment of OSA.

15. A composition comprising Δ-9-tetrahydrocannabinol (THC) or a pharmaceutically acceptable salt thereof, and acetazolamide or a pharmaceutically acceptable salt thereof.

* * * * *